United States Patent
Lee et al.

(10) Patent No.: US 10,647,686 B2
(45) Date of Patent: May 12, 2020

(54) SUBSTITUTED PYRIMIDINES FOR PREVENTING OR TREATING CANCER AND INFLAMMATORY DISEASES

(71) Applicant: KOREA RESEARCH INSTITUTE OF CHEMICAL TECHNOLOGY, Daejeon (KR)

(72) Inventors: Kwangho Lee, Daejeon (KR); Gildon Choi, Daejeon (KR); Na Ri Lee, Iksan-si (KR); Sang Jun Park, Cheongju-si (KR); Myoung Eun Jung, Daejeon (KR); Seong Jin Kim, Seoul (KR); Kyung-Min Yang, Incheon (KR); Jihee Lee, Yongin-si (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 0 days.

(21) Appl. No.: 16/347,480

(22) PCT Filed: Nov. 1, 2017

(86) PCT No.: PCT/KR2017/012222
§ 371 (c)(1),
(2) Date: May 3, 2019

(87) PCT Pub. No.: WO2018/088749
PCT Pub. Date: May 17, 2018

(65) Prior Publication Data
US 2019/0284143 A1    Sep. 19, 2019

(30) Foreign Application Priority Data

Nov. 8, 2016 (KR) .......................... 10-2016-0147977

(51) Int. Cl.
*A61K 31/505* (2006.01)
*C07D 239/48* (2006.01)
(Continued)

(52) U.S. Cl.
CPC .......... *C07D 239/48* (2013.01); *A61K 9/0019* (2013.01); *A61K 9/14* (2013.01);
(Continued)

(58) Field of Classification Search
CPC .............................. A61K 31/505; C07D 239/48
(Continued)

(56) References Cited

U.S. PATENT DOCUMENTS

2011/0098280 A1    4/2011 Garcia-Echeverria et al.

FOREIGN PATENT DOCUMENTS

| CN | 101506176 A | 8/2009 |
| GB | 1092571 A | 11/1967 |

(Continued)

OTHER PUBLICATIONS

Massague et al., "Smad transcription factors", Genes & Development, 2005, vol. 19, pp. 2783-2810.
(Continued)

*Primary Examiner* — Douglas M Willis
(74) *Attorney, Agent, or Firm* — Lucas & Mercanti, LLP

(57) ABSTRACT

The present invention relates to compounds represented by Formula 1

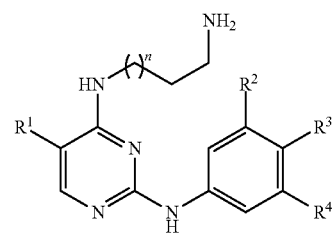

Formula 1 or a pharmaceutically acceptable salt thereof,
wherein:
$R^1$ is chloro or methyl;
$R^2$ is hydrogen or chloro;
$R^3$ is hydrogen, fluoro, chloro, bromo, methyl, ethyl, isopropyl, pentyl, hexyl, octyl, methoxy, phenoxy, (4-nitrophenyl)sulfonyl, piperidin-4-yl, or piperazin-1-yl;
$R^4$ is hydrogen, chloro, methyl or trifluoromethyl, phenoxy, (4-nitrophenyl)sulfonyl or piperidin-4-yl; or
$R^3$ and $R^4$, together with the carbons to which they are attached, form a fused ring selected form the group consisting of:

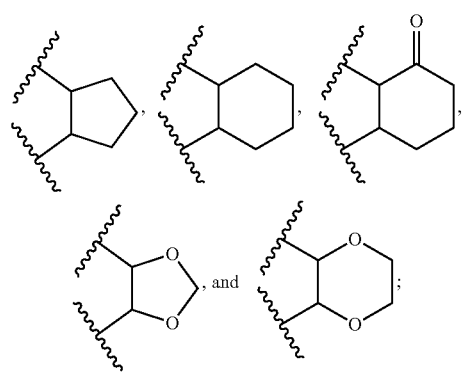

n is 1 or 2.
These compounds according to the present invention remarkably inhibits activity of DRAK that inhibits signal
(Continued)

systems of TGF-β, which is known to suppress cancer growth, and thus the novel pyrimidine compounds can be used as a pharmaceutical composition for preventing or treating cancer and can be used as a pharmaceutical composition for preventing or treating inflammatory disease.

10 Claims, No Drawings

(51) Int. Cl.
*A61K 9/00* (2006.01)
*A61K 9/14* (2006.01)
*A61K 9/20* (2006.01)
*A61K 9/48* (2006.01)
*C07D 405/12* (2006.01)

(52) U.S. Cl.
CPC .......... *A61K 9/2013* (2013.01); *A61K 9/2018* (2013.01); *A61K 9/2059* (2013.01); *A61K 9/4825* (2013.01); *A61K 31/505* (2013.01); *C07D 405/12* (2013.01)

(58) Field of Classification Search
USPC .......................................... 514/275; 544/323
See application file for complete search history.

(56) References Cited

FOREIGN PATENT DOCUMENTS

| | | |
|---|---|---|
| KR | 10-2013-0090144 A | 8/2013 |
| KR | 10-2015-0087271 A | 7/2015 |
| WO | 2007146977 A1 | 12/2007 |

OTHER PUBLICATIONS

International Search Report for Corresponding International Application No. PCT/KR2017/012222 (3 Pages) (dated Feb. 5, 2018).

SUBSTITUTED PYRIMIDINES FOR PREVENTING OR TREATING CANCER AND INFLAMMATORY DISEASES

CROSS REFERENCE TO RELATED APPLICATIONS

This application is a 371 of PCT/KR2017/012222, filed Nov. 1, 2017, which claims the benefit of priority from Korean Patent Application No. 10-2016-0147977, filed Nov. 8, 2016, the contents of each of which are incorporated herein by reference.

BACKGROUND OF THE INVENTION

Field of the Invention

The present invention relates to novel pyrimidine compounds, a method for preparing the same, and a pharmaceutical composition containing the same as an active ingredient for preventing or treating cancer and inflammatory disease.

Description of the Related Art

TGF-β (Transforming growth factor-β) is a cytokine that regulates various in vivo physiological processes such as cell proliferation, differentiation, apoptosis, migration, extracellular matrix (ECM) production, angiogenesis and development, etc. The active TGF-β is in the form of a 25 kDa dimer. Once this cytokine is secreted by cells and activated, it binds to a serine/threonine receptor kinase on the cell membrane, by which a signal is transmitted. The TGF-β receptor on the cell membranes is composed of Type I and Type II. When the receptor binds to TGF-β, the two types of receptors form a heterotetrameric complex, and the all time active Type II receptor phosphorylates the Type I receptor, resulting in the activation of kinases.

In the signal transduction mediated by TGF-beta, the mediator to transmit an extracellular signal into the nucleus is a transcription factor called Smad. The Type I receptor phosphorylated by the Type II receptor phosphorylate and activate Smad. The phosphorylated Smad protein enters in the nucleus and cooperates with transcription factors therein to regulate the expression of various genes (Masque J. Seoane J, Wotton D. Gene Dev 19: 2783-2810, 2005.).

The cell response to TGF-β varies depending on the type of the cells and the stimulation conditions, such as promoting or inhibiting proliferation, cell death, and differentiation, etc. Cytokines belonging to the TGF-β family use various Type I and Type II receptors. Up to now, 7 kinds of Type I receptors called ALK (activin receptor-like kinase) have been identified and 5 kinds of Type II receptors have been identified. In most cell types, TGF-β uses ALK5 and TR-2 (testicular receptor-2) receptors.

8 kinds of Smad proteins have been identified, which are divided into three groups according to the function such as receptor-activated Smad (R-Smad, Smad1, Smad2, Smad3, Smad5, and Smad8), common mediator Smad (Co-Smad, Smad4) and inhibitory Smad (1-Smad, Smad6, and Smad 7). In general, TGF-β/Activin/Nodal group uses Smad 2 and Smad 3, and BMP/GDF/MIS group uses Smad1, Smad5 and Smad8 of R-Smad. When a ligand binds, the Type I receptor directly phosphorylates SSXS motif at the carboxy terminal of R-Smad, and the phosphorylated R-Smad binds to Smad4, which is Co-Smad, which enters in the nucleus and binds to Smad binding element (SBE) on DNA. SBE often becomes a binding site for other transcription factors, indicating that Smad protein binds to other transcription factors and cooperates with them to regulate gene expression. Unlike R-Smad and Co-Smad, I-Smad (Smad6, 7) does not have the carboxy terminal which is phosphorylated by Type I receptor and inhibits TGF-β signaling. The most well known cell response to TGF-β is the arrest of cell growth. TGF-β induces growth arrest in epithelial cells, endothelial cells, blood cells, and neurons. Stimulation of TGF-β induces signal transduction at any stage of cell cycle but induces arrest of G1 cell cycle.

Stimulation of TGF-β in epithelial cells induces transcription of cyclin-dependent kinase inhibitors such as p21Cip1/WAF1 and p15Ink4b, and thereby activates antiproliferative responses and induces arrest of G1 cell cycle. In addition, TGF-β inhibits transcription of the growth factor and the degradation inhibitors ld1, ld2 and ld3. Furthermore, TGF-β, is known to induce various cell death responses.

As described above, TGF-β, and its signal transduction mediator Smad are the elements playing an important role not only in physiological functions such as cell growth, development, and differentiation but also in development and progress of various diseases such as cancer and fibrosis. Therefore, studies on active systems for regulating the signal transduction and methods for screening thereof have been actively conducted.

On the other hand, a protein kinase is one of phorphotransferases, which is a catalytic enzyme inducing phosphorylation of the hydroxyl group of serine, threonine or thyrosine. In the signal transduction system, a receptor thyrosine kinase plays an important role in cell growth and proliferation, but can be a cause of various diseases when it is abnormally activated by various reasons such as gene overexpression, gene mutation and gene amplification, etc, because of which it has been a major target of the development of therapeutic agents.

DRAK (Death-associated protein-kinase-Related Apoptosis Kinase) is a protein involved in TGF-β signal transduction, and it becomes active by forming a homodimer as a serine/threonine kinase.

DRAK1 and DRAK2-mediated TGF-β is involved in basic cellular functions such as cell proliferation, differentiation, migration and apoptosis, as mentioned above. The TGF-β ligand transmits signals by binding to Type I and Type II TGF-β receptors, the serine/threonine kinases, and activates the expression of TGF-β specific gene involved in cell growth inhibition by using the Type I TGF-β receptor substrate Smad 2 and Smad 3 as a mediator. At t his time, in order to maintain homeostasis of cells by the TGF-β signal transduction system, Smad6 and Smad7 proteins play a role in suppressing TGF-β signaling. As a result of the TGF-β signaling, cell growth is suppressed and tumor can be inhibited.

Unlike normal cells, cancer cells display resistance against TGF-β, which seems to be attributed to the overexpression of negative regulators such as Smad 7, TMEPA I and FKBP 12, known to be involved in inhibitory/negative feedback loop to control the TGF-β/Smads signal transduction pathway.

To understand the TGF-β related diseases, it is necessary to develop a novel regulator in addition to the known negative regulators of the TGF-β signal transduction system.

In a recent paper in Cell Report, it was reported that DRAK2 (Death-associated protein-kinase-Related Apoptosis Kinase 2), a serine/threonine kinase involved in T cell activation and autoimmune disease, binds to Type I TGF-β receptor, which was confirmed in the course of identifying a protein binding to TGF-β receptor by using yeast two hybrid system. It was also confirmed that DRAK2 inhibits TGF-β/Smads signaling negatively by binding to Type I TGF-β receptor in epithelial cell carcinoma, resulting in the intervention of the cancer formation inhibitory ability of TGF-β.

The function of DRAK1 and DRAK2 proteins was focused on immune system diseases, but the necessity of study in more various tissues was suggested. Particularly, these proteins functioning as a novel antagonist of TGF-β signaling can be a promising target for the development of a therapeutic agent for TGF-β related diseases.

Thus, the present inventors have been tried to develop a compound that shows DRAK activity inhibitory effect. As a result, the present inventors confirmed that the pyrimidine compounds of the invention and its pharmaceutically acceptable salt can be functioning as a DRAK inhibitor so that it can be used as a preventive or therapeutic agent for cancer and inflammatory disease, leading to the completion of the present invention.

SUMMARY OF THE INVENTION

It is an object of the present invention to provide novel pyrimidine compounds or a pharmaceutically acceptable salt thereof.

It is another object of the present invention to provide a preparation method of the novel pyrimidine compounds above.

It is also an object of the present invention to provide a pharmaceutical composition comprising the novel pyrimidine compounds or the pharmaceutically acceptable salt thereof as an active ingredient for the prevention or treatment of cancer.

It is further an object of the present invention to provide a pharmaceutical composition comprising the novel pyrimidine compounds or the pharmaceutically acceptable salt thereof as an active ingredient for the prevention or treatment of inflammatory disease.

It is also an object of the present invention to provide a health functional food comprising the novel pyrimidine compounds or the pharmaceutically acceptable salt thereof as an active ingredient for the prevention or amelioration of cancer.

To achieve the above objects, the present invention provides a compound represented by formula 1 below or a pharmaceutically acceptable salt thereof:

[Formula 1]

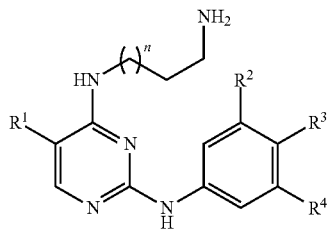

In formula 1,
n is an integer of 1 or 2;
$R^1$ is —H, halogen, or $C_{1-10}$ straight or branched alkyl;
$R^2$ is —H or halogen;
$R^3$ is —H, halogen, $C_{1-10}$ straight or branched alkyl, $C_{1-10}$ straight or branched alkoxy,

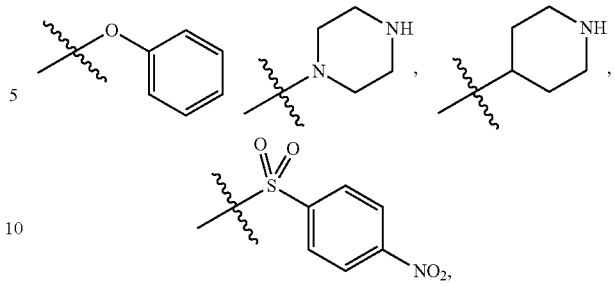

or with $R^4$ and each neighboring carbon to form

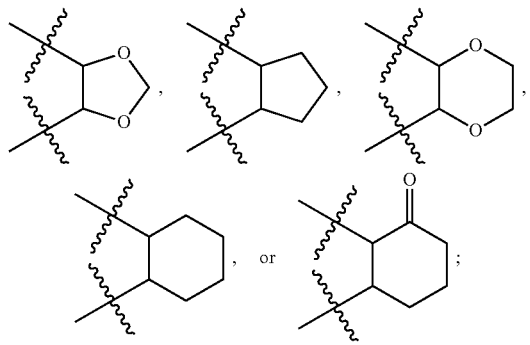

and
$R^4$ is —H, halogen or $C_{1-10}$ straight or branched alkyl nonsubstituted or substituted with one or more halogens.

The present invention also provides a preparation method of the compound represented by formula 1 above, which comprises the steps of preparing the compound represented by formula 4 by reacting the compound represented by formula 2 with the compound represented by formula 3 (step 1); and preparing the compound represented by formula 1 by reacting the compound represented by formula 4 prepared in step 1 above with the compound represented by formula 5 in the presence of an acid (step 2), as shown in reaction formula 1 below.

[Reaction Formula 1]

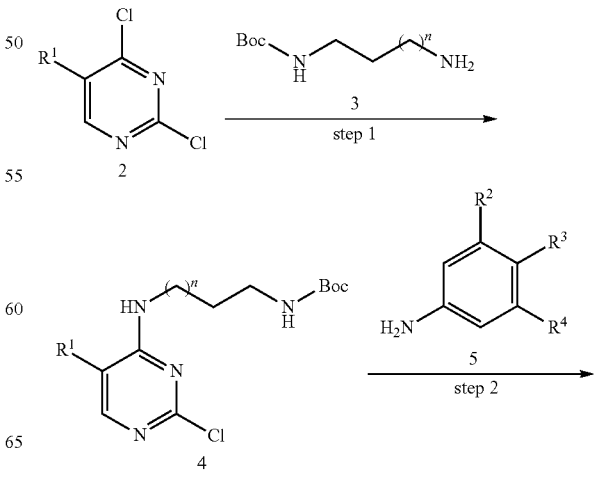

-continued

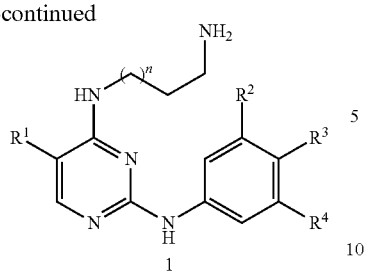

1

In reaction formula 1, n, $R^1$, $R^2$, $R^3$, and $R^4$ are independently as defined in formula 1.

Further, the present invention provides a pharmaceutical composition comprising the compound represented by formula 1 above or the pharmaceutically acceptable salt thereof as an active ingredient for the prevention or treatment of cancer.

The present invention also provides a pharmaceutical composition comprising the compound represented by formula 1 above or the pharmaceutically acceptable salt thereof as an active ingredient for the prevention or treatment of inflammatory disease.

The present invention also provides a health functional food comprising the compound represented by formula 1 above or the pharmaceutically acceptable salt thereof as an active ingredient for the prevention or amelioration of cancer.

The present invention also provides a method for preventing or treating cancer comprising the step of administering a pharmaceutical composition or a health functional food comprising the compound represented by formula 1 above or the pharmaceutically acceptable salt thereof as an active ingredient to a subject in need.

The present invention also provides a use of the pharmaceutical composition or the health functional food comprising the compound represented by formula 1 above or the pharmaceutically acceptable salt thereof as an active ingredient for the prevention or treatment of cancer.

The present invention also provides a method for preventing or treating inflammatory disease comprising the step of administering a pharmaceutical composition or a health functional food comprising the compound represented by formula 1 above or the pharmaceutically acceptable salt thereof as an active ingredient to a subject in need.

In addition, the present invention provides a use of the pharmaceutical composition or the health functional food comprising the compound represented by formula 1 above or the pharmaceutically acceptable salt thereof as an active ingredient for the prevention or treatment of inflammatory disease.

ADVANTAGEOUS EFFECT

The novel pyrimidine compounds of the present invention significantly inhibit the activity of DRAK known to interfere the TGF-β signal transduction system playing a role in inhibiting cancer growth. Therefore, it can be used as a pharmaceutical composition for preventing or treating cancer and inflammatory disease.

DESCRIPTION OF THE PREFERRED EMBODIMENTS

Hereinafter, the present invention is described in detail.

The present invention provides a compound represented by formula 1 below or a pharmaceutically acceptable salt thereof:

[Formula 1]

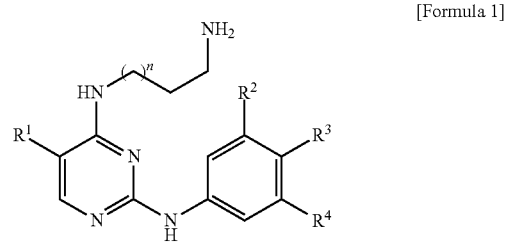

In formula 1, n is an integer of 1 or 2;

$R^1$ is —H, halogen, or $C_{1-10}$ straight or branched alkyl;

$R^2$ is —H or halogen;

$R^3$ is —H, halogen, $C_{1-10}$ straight or branched alkyl, $C_{1-10}$ straight or branched alkoxy,

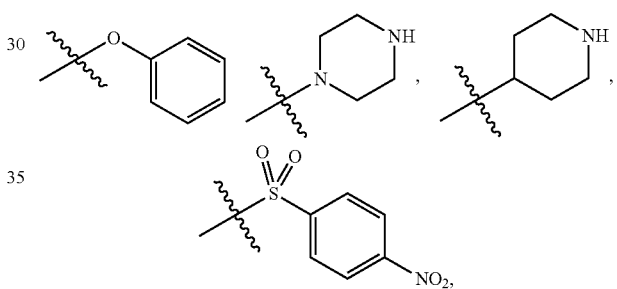

or with $R^4$ and each neighboring carbon to form

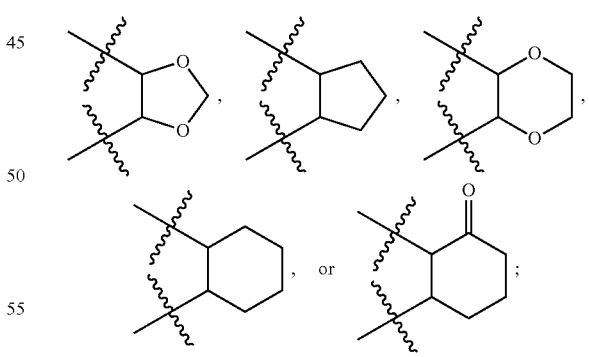

and $R^4$ is —H, halogen or $C_{1-10}$ straight or branched alkyl nonsubstituted or substituted with one or more halogens.

Preferably, n is an integer of 1 or 2;

$R^1$ is —H, halogen, or $C_{1-8}$ straight or branched alkyl;

$R^2$ is —H or halogen;

$R^3$ is —H, halogen, $C_{1-8}$ straight or branched alkyl, $C_{1-8}$ straight or branched alkoxy,

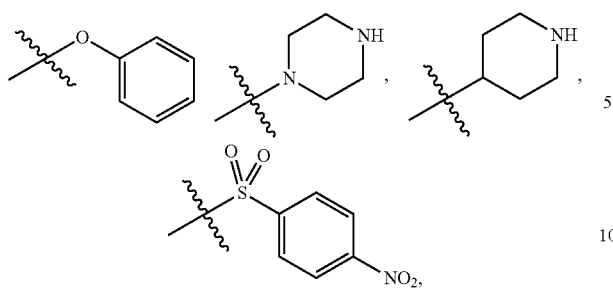

or with R⁴ and each neighboring carbon to form

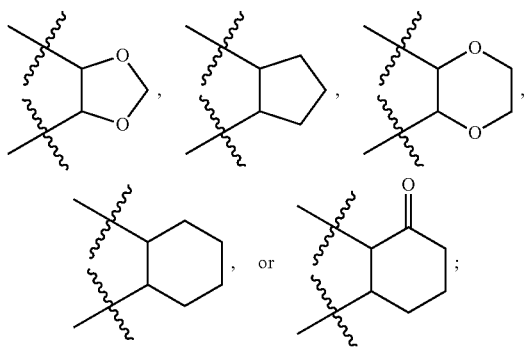

and

R⁴ is —H, halogen or $C_{1-8}$ straight or branched alkyl nonsubstituted or substituted with one or more halogens.

More preferably, n is an integer of 1 or 2;

R¹ is —H, —Cl or —CH₃;

R² is —H or —Cl;

R³ is —H, —F, —Cl, —Br, methyl, ethyl, isopropyl, pentyl, hexyl, octyl, —OCH₃,

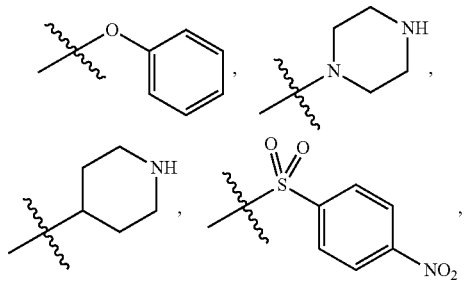

or with R⁴ and each neighboring carbon to form

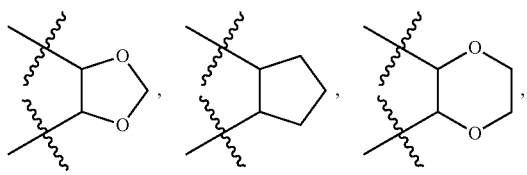

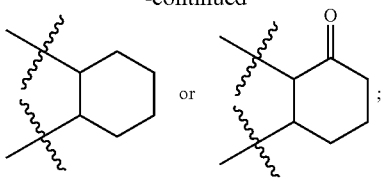

and

R⁴ is —H, —Cl, —CH₃ or —CF₃.

Most preferably, the compound represented by formula 1 above is selected from the group consisting of the following compounds:

(1) N4-(3-aminopropyl)-5-chloro-N2-(4-chlorophenyl)pyrimidine-2,4-diamine;
(2) N4-(3-aminopropyl)-5-chloro-N2-(3,5-dichlorophenyl)pyrimidine-2,4-diamine;
(3) N4-(3-aminopropyl)-5-chloro-N2-(4-isopropylphenyl)pyrimidine-2,4-diamine;
(4) N4-(3-aminopropyl)-5-chloro-N2-(4-pentylphenyl)pyrimidine-2,4-diamine;
(5) N4-(3-aminopropyl)-5-chloro-N2-(4-octylphenyl)pyrimidine-2,4-diamine;
(6) N4-(3-aminopropyl)-5-chloro-N2-(3-chloro-4-methylphenyl)pyrimidine-2,4-diamine;
(7) N4-(3-aminopropyl)-5-chloro-N2-(3-chloro-4-fluorophenyl)pyrimidine-2,4-diamine;
(8) N4-(3-aminopropyl)-5-chloro-N2-(3,4-dichlorophenyl)pyrimidine-2,4-diamine;
(9) N4-(3-aminopropyl)-5-chloro-N2-(4-fluorophenyl)pyrimidine-2,4-diamine;
(10) N4-(3-aminopropyl)-5-chloro-N2-(4-phenoxyphenyl)pyrimidine-2,4-diamine;
(11) N4-(3-aminopropyl)-5-chloro-N2-(4-ethylphenyl)pyrimidine-2,4-diamine;
(12) N4-(3-aminopropyl)-5-chloro-N2-(4-hexylphenyl)pyrimidine-2,4-diamine;
(13) N4-(3-aminopropyl)-5-chloro-N2-(4-(4-nitrophenylsulfonyl)phenyl)pyrimidine-2,4-diamine;
(14) N4-(3-aminopropyl)-5-chloro-N2-(3,4-dimethylphenyl)pyrimidine-2,4-diamine
(15) N4-(3-aminopropyl)-5-chloro-N2-(4-fluoro-3-(trifluoromethyl)phenyl)pyrimidine-2,4-diamine;
(16) N4-(3-aminopropyl)-N2-(4-bromo-3-(trifluoromethyl)phenyl)-5-chloropyrimidine-2,4-diamine;
(17) N4-(3-aminopropyl)-N2-(4-bromophenyl)-5-chloropyrimidine-2,4-diamine;
(18) N4-(3-aminopropyl)-5-chloro-N2-(3-chloro-4-methoxyphenyl)pyrimidine-2,4-diamine;
(19) N4-(3-aminopropyl)-N2-(4-chlorophenyl)-5-methylpyrimidine-2,4-diamine;
(20) N4-(3-aminopropyl)-N2-(benzo[d][1,3]dioxol-5-yl)-5-chloropyrimidine-2,4-diamine;
(21) N4-(3-aminopropyl)-5-chloro-N2-(2,3-dihydro-1H-indene-5-yl)pyrimidine-2,4-diamine;
(22) N4-(3-aminopropyl)-5-chloro-N2-(2,3-dihydrobenzo[b][1,4]dioxin-6-yl)pyrimidine-2,4-diamine;
(23) N4-(3-aminopropyl)-5-chloro-N2-(5,6,7,8-tetrahydronaphthalene-2-yl)pyrimidine-2,4-diamine;
(24) 6-(4-(3-aminopropylamino)-5-chloropyrimidine-2-ylamino)-3,4-dihydronaphthalene-1(2H)-one;
(25) N4-(3-aminopropyl)-5-chloro-N2-(4-(piperazine-1-yl)phenyl)pyrimidine-2,4-diamine;
(26) N4-(3-aminopropyl)-5-chloro-N2-(4-(piperidine-4-yl)phenyl)pyrimidine-2,4-diamine;

(27) N4-(3-aminopropyl)-N2-(3-chloro-4-methylphenyl)-5-methylpyrimidine-2,4-diamine;
(28) N4-(3-aminopropyl)-N2-(4-fluorophenyl)-5-methylpyrimidine-2,4-diamine;
(29) N4-(3-aminopropyl)-5-methyl-N2-(4-(piperazine-1-yl)phenyl)pyrimidine-2,4-diamine;
(30) N4-(3-aminopropyl)-5-methyl-N2-(5,6,7,8-tetrahydronaphthalene-2-yl)pyrimidine-2,4-diamine;
(31) N4-(3-aminopropyl)-N2-(4-fluoro-3-(trifluoromethyl)phenyl)-5-methylpyrimidine-2,4-diamine;
(32) N4-(3-aminopropyl)-N2-(4-bromo-3-(trifluoromethyl)phenyl)-5-methylpyrimidine-2,4-diamine;
(33) N4-(3-aminopropyl)-5-methyl-N2-(4-phenoxyphenyl)pyrimidine-2,4-diamine;
(34) N4-(3-aminopropyl)-5-methyl-N2-(4-(4-nitrophenylsulfonyl)phenyl)pyrimidine-2,4-diamine;
(35) N4-(3-aminopropyl)-N2-(4-bromophenyl)-5-methylpyrimidine-2,4-diamine;
(36) N4-(3-aminopropyl)-N2-(2,3-dihydrobenzo[b][1,4]dioxin-6-yl)-5-methylpyrimidine-2,4-diamine;
(37) N4-(3-aminopropyl)-N2-(3,4-dimethylphenyl)-5-methylpyrimidine-2,4-diamine;
(38) N4-(3-aminopropyl)-N2-(3-chloro-4-fluorophenyl)-5-methylpyrimidine-2,4-diamine;
(39) N4-(3-aminopropyl)-N2-(3,4-dichlorophenyl)-5-methylpyrimidine-2,4-diamine;
(40) N4-(4-n-aminobutyl)-N2-(4-chlorophenyl)-5-chloropyrimidine-2,4-diamine; and
(41) N4-(4-n-aminobutyl)-N2-(3,5-dichlorophenyl)-5-chloropyrimidine-2,4-diamine.

The compound represented by formula 1 of the present invention can be used as a form of a pharmaceutically acceptable salt, in which the salt is preferably acid addition salt formed by pharmaceutically acceptable free acids. The acid addition salt herein can be obtained from inorganic acids such as hydrochloric acid, nitric acid, phosphoric acid, sulfuric acid, hydrobromic acid, hydroiodic acid, nitrous acid, and phosphorous acid; non-toxic organic acids such as aliphatic mono/dicarboxylate, phenyl-substituted alkanoate, hydroxy alkanoate, alkandioate, aromatic acids, and aliphatic/aromatic sulfonic acids; or organic acids such as acetic acid, benzoic acid, citric acid, lactic acid, maleic acid, gluconic acid, methanesulfonic acid, 4-toluenesulfonic acid, tartaric acid, and fumaric acid. The pharmaceutically non-toxic salts are exemplified by sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, cabacate, fumarate, maliate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, hydroxybutylate, glycolate, malate, tartrate, methanesulfonate, propanesulfonate, naphthalene-1-sulfonate, naphthalene-2-sulfonate, and mandelate.

The acid addition salt in this invention can be prepared by the conventional method known to those in the art. For example, the derivative represented by formula 1 is dissolved in an organic solvent such as methanol, ethanol, acetone, dichloromethane, and acetonitrile, to which organic acid or inorganic acid is added to induce precipitation. Then, the precipitate is filtered and dried to give the salt. Or the solvent and the excessive acid are distillated under reduced pressure, and dried to give the salt. Or the precipitate is crystallized in an organic solvent to give the same.

A pharmaceutically acceptable metal salt can be prepared by using a base. Alkali metal or alkali earth metal salt is obtained by the following processes: dissolving the compound in excessive alkali metal hydroxide or alkali earth metal hydroxide solution; filtering non-soluble compound salt; evaporating the remaining solution and drying thereof. At this time, the metal salt is preferably prepared in the pharmaceutically suitable form of sodium, potassium, or calcium salt. And the corresponding silver salt is prepared by the reaction of alkali metal or alkali earth metal salt with proper silver salt (ex; silver nitrate).

The present invention includes not only the compound represented by formula 1 but also a pharmaceutically acceptable salt thereof, and a solvate, a stereoisomer, or a hydrate possibly produced from the same.

The present invention also provides a preparation method of the compound represented by formula 1 above, which comprises the steps of preparing the compound represented by formula 4 by reacting the compound represented by formula 2 with the compound represented by formula 3 (step 1); and preparing the compound represented by formula 1 by reacting the compound represented by formula 4 prepared in step 1 above with the compound represented by formula 5 in the presence of an acid (step 2), as shown in reaction formula 1 below.

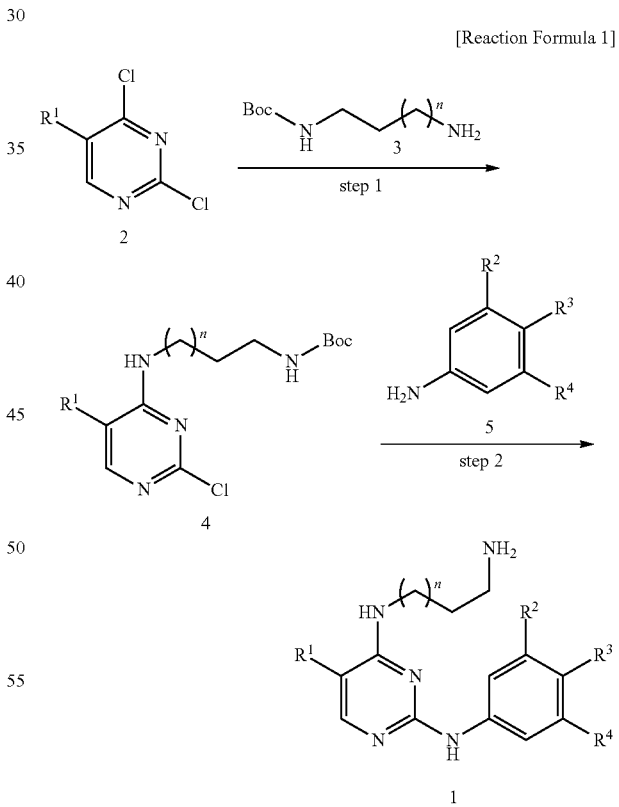

[Reaction Formula 1]

In reaction formula 1,
n, $R^1$, $R^2$, $R^3$, and $R^4$ are independently as defined in formula 1.

Hereinafter, the preparation method of the compound represented by formula 1 of the present invention is described in more detail, step by step.

In the preparation method of the compound represented by formula 1 of the present invention, step 1 is to prepare the compound represented by formula 4 by reacting the compound represented by formula 2 with the compound represented by formula 3.

At this time, the reaction temperature is not particularly limited but the reaction can be performed at 0° C.~100° C., preferably at 10° C.~70° C., more preferably at 20° C.~40° C. and most preferably at 25° C.

The reaction time is not particularly limited, either, but the reaction can be performed for 1~10 hours, preferably for 2~8 hours, more preferably for 3~6 hours and most preferably for 5 hours.

In the preparation method of the compound represented by formula 1 according to the present invention, step 2 is to prepare the compound represented by formula 1 by reacting the compound represented by formula 4 prepared in step 1 above with the compound represented by formula 5. At this time, the reaction temperature is not particularly limited but the reaction can be performed at 30° C.~150° C., preferably at 50° C.~140° C., more preferably at 60° C.~120° C. and most preferably at 100° C.

The reaction time is not particularly limited, either, but the reaction can be performed for 6~20 hours, preferably for 10~18 hours, more preferably for 12~18 hours and most preferably for 16 hours.

The acid can be used without limitation if it is an acid capable of deprotection of -Boc, for example hydrochloric acid.

The present invention also provides a pharmaceutical composition comprising the compound represented by formula 1 above or the pharmaceutically acceptable salt thereof as an active ingredient for the prevention or treatment of cancer. Herein, the cancer is selected from the group consisting of pseudomyxoma, intrahepatic cholangiocarcinoma, hepatoblastoma, liver cancer, thyroid cancer, colon cancer, testicular cancer, myelodysplastic syndrome, glioblastoma, oral cancer, lip cancer, mycosis fungoides, acute myelogenous leukemia, acute lymphocytic leukemia, basal cell carcinoma, ovarian epithelial cancer, ovarian germ cell carcinoma, male breast cancer, brain cancer, pituitary adenoma, multiple myeloma, gallbladder cancer, biliary cancer, colon cancer, chronic myelogenous leukemia, chronic lymphocytic leukemia, retinoblastoma, choroidal melanoma, diffuse large B cell lymphoma, ampulla of Vater cancer, bladder cancer, peritoneal cancer, parathyroid cancer, adrenal gland cancer, sinunasal cancer, non-small cell lung cancer, non-Hodgkin's lymphoma, tongue cancer, astrocytoma, small cell lung cancer, pediatric brain cancer, pediatric lymphoma, childhood leukemia, small bowel cancer, meningioma, esophagus cancer, glioma, neuroblastoma, renal cancer, kidney cancer, heart cancer, duodenal cancer, malignant soft tissue tumor, malignant bone cancer, malignant lymphoma, malignant mesothelioma, malignant melanoma, eye cancer, vulvar cancer, ureteral cancer, urethral cancer, cancer of unknown primary site, gastric lymphoma, gastric cancer, gastric carcinoid, gastrointestinal stromal cancer, Wilms' tumor, breast cancer, sarcoma, penile cancer, pharyngeal cancer, getstational trophoblastic disease, cervical cancer, endometrial cancer, uterine sarcoma, prostate cancer, metastatic bone cancer, metastatic brain cancer, mediastinal cancer, rectal cancer, rectal carcinoid, vaginal cancer, spinal cord cancer, vestibular schwannoma, pancreatic cancer, salivary gland cancer, Kaposi's sarcoma, Paget's disease, tonsil cancer, squamous cell carcinoma, adenocarcinoma of lung, lung cancer, squamos cell carcinoma of lung, skin cancer, anal cancer, rhabdomyosarcoma, laryngeal cancer, pleural cancer, and thymus cancer.

The present invention also provides a pharmaceutical composition comprising the compound represented by formula 1 above or the pharmaceutically acceptable salt thereof as an active ingredient for the prevention or treatment of inflammatory disease. Herein, the inflammatory disease is selected from the group consisting of inflammatory colitis of autoimmune diseases, Crohn's disease, Behcet's disease, multiple sclerosis, macular degeneration, arthritis, type 1 diabetes, encephalitis and viral meningitis.

The compound represented by formula 1 according to the present invention can be prepared for oral or parenteral administration by mixing with generally used diluents or excipients such as fillers, extenders, binders, wetting agents, disintegrating agents and surfactants.

The formulations for oral administration are exemplified by tablets, pills, hard/soft capsules, solutions, suspensions, emulsions, syrups, granules, and elixirs, etc. These formulations can include diluents (for example, lactose, dextrose, sucrose, mannitol, sorbitol, cellulose, and/or glycine) and lubricants (for example, silica, talc, stearate and its magnesium or calcium salt, and/or polyethylene glycol) in addition to the active ingredient. Tablets can include binding agents such as magnesium aluminum silicate, starch paste, gelatin, methylcellulose, sodium carboxymethylcellulose and/or polyvinylpyrolidone, and if necessary disintegrating agents such as starch, agarose, alginic acid or its sodium salt or azeotropic mixtures and/or absorbents, coloring agents, flavors, and sweeteners can be additionally included thereto.

The pharmaceutical composition comprising the compound represented by formula 1 as an active ingredient can be administered parenterally and the parenteral administration includes subcutaneous injection, intravenous injection, intramuscular injection and intrathoracic injection.

To prepare the composition as a formulation for parenteral administration, the compound represented by formula 1 or the pharmaceutically acceptable salt thereof is mixed with a stabilizer or a buffering agent to produce a solution or a suspension, which is then formulated as ampoules or vials. The composition herein can be sterilized and additionally contains preservatives, stabilizers, wettable powders or emulsifiers, salts and/or buffers for the regulation of osmotic pressure, and other therapeutically useful materials, and the composition can be formulated by the conventional mixing, granulating or coating method.

The effective dosage of the pharmaceutical composition comprising the compound represented by formula 1 or the pharmaceutically acceptable salt thereof of the present invention can vary depending on the patient's age, weight, gender, administration form, health condition and disease severity. Based on an adult patient weighing 70 kg, the dosage is generally 0.1~1000 mg/day, and preferably 1~500 mg/day. The composition of the present invention can be administered once or several times a day at a predetermined time interval according to the judgment of a doctor or a pharmacist.

The present invention also provides a health functional food comprising the compound represented by formula 1 above or the pharmaceutically acceptable salt thereof as an active ingredient for the prevention or amelioration of cancer.

The present invention also provides a method for preventing or treating cancer comprising the step of administering the pharmaceutical composition or the health functional food comprising the compound represented by formula 1 above or the pharmaceutically acceptable salt thereof as an active ingredient to a subject in need.

The present invention also provides a use of the pharmaceutical composition or the health functional food comprising the compound represented by formula 1 above or the pharmaceutically acceptable salt thereof as an active ingredient for the prevention or treatment of cancer.

The present invention also provides a method for preventing or treating inflammatory disease comprising the step of administering a pharmaceutical composition or a health functional food comprising the compound represented by formula 1 above or the pharmaceutically acceptable salt thereof as an active ingredient to a subject in need.

In addition, the present invention provides a use of the pharmaceutical composition or the health functional food comprising the compound represented by formula 1 above or the pharmaceutically acceptable salt thereof as an active ingredient for the prevention or treatment of inflammatory disease.

The novel pyrimidine compounds of the present invention displays a remarkably excellent DRAK inhibitory activity at a low concentration, so that it can be effectively used as a pharmaceutical composition for the prevention or treatment of cancer and inflammatory disease, which has been supported by the following experiments.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Preparation of N4-(3-aminopropyl)-5-chloro-N2-(4-chlorophenyl)pyrimidine-2,4-diamine

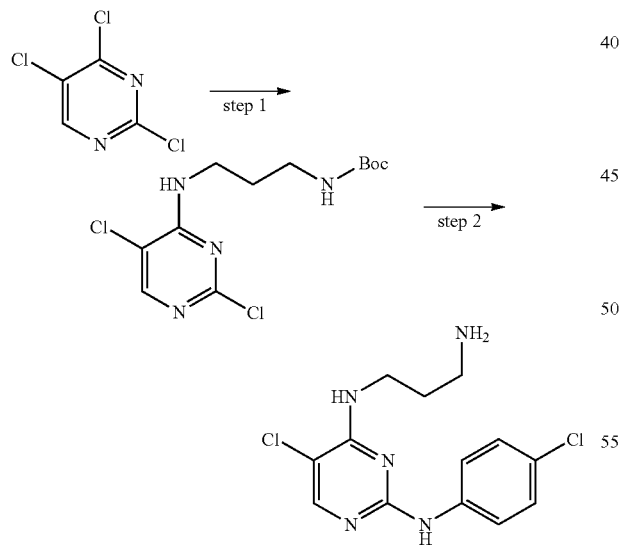

Step 1: Preparation of tert-butyl (3-((2,5-dichloropyrimidine-4-yl)amino)propyl)carbamate 2,4,5-Trichloropyrimidine (5.7 mmol, 1.05 g) was added to isopropanol (40 mL) at 0° C., followed by stirring. Tert-butyl (3-aminopropyl) carbamate (5.7 mmol, 1 g) and triethylamine (TEA) (29 mmol, 4 mL) were slowly added thereto, which was reacted at room temperature for 5 hours. Upon completion of the reaction, the reaction mixture was cooled down at room temperature, and then the solvent was eliminated under reduced pressure. The mixture was separated by mplc (medium pressure liquid chromatography). As a result, tert-butyl (3-((2,5-dichloropyrimidine-4-yl)amino)propyl)carbamate was obtained as a white solid with the yield of 89%.

$^1$H NMR (CDCl$_3$, 300 MHz) δ 7.99 (br s, 1H), 6.46 (br s, 1H), 4.85 (br s, 1H), 3.58 (m, 2H), 3.21 (m, 2H), 1.73 (m, 2H), 1.45 (s, 9H);

Mass (M+H$^+$) calcd for C$_{12}$H$_{18}$Cl$_2$N$_4$O$_2$ 320.1, found 321.1.

Step 2: Preparation of N4-(3-aminopropyl)-5-chloro-N2-(4-chlorophenyl)pyrimidine-2,4-diamine Tert-butyl (3-((2,5-dichloropyrimidine-4-yl)amino)propyl)carbamate (0.27 mmol, 86 mg) and 4-chlorobenzeneamine (0.54 mmol, 87 mg) were dissolved in 2-ethoxyethanol containing 0.08 N HCl, followed by heating at 100° C. for 16 hours. Upon completion of the reaction, the mixture was cooled down at room temperature and the solvent was eliminated under reduced pressure. The mixture was separated by prep TLC (Preparative Thin-Layer (Planar) Chromatography). As a result, N4-(3-aminopropyl)-5-chloro-N2-(4-chlorophenyl)pyrimidine-2,4-diamine was obtained as a solid with yield of 40%.

$^1$H NMR (DMSO-d6, 300 MHz) δ 10.30 (br s, 1H), 8.32 (br s, 1H), 8.15 (s, 1H), 7.98 (br s, 2H), 7.67 (d, J=8.70 Hz, 2H), 7.40 (d, J=8.76 Hz, 2H), 3.50 (m, 2H), 2.79 (m, 2H), 1.89 (m, 2H);

Mass (M+H$^+$) calcd for C$_{13}$H$_{15}$C$_{12}$N$_5$ 311.0, found 312.1.

Example 2: Preparation of N4-(3-aminopropyl)-5-chloro-N2-(3,5-dichlorophenyl)pyrimidine-2,4-diamine

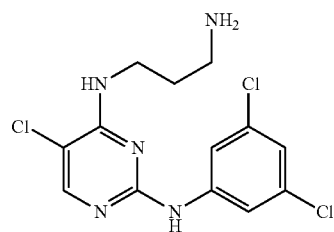 [SMILES: NCCCNc1nc(Nc2cc(Cl)cc(Cl)c2)ncc1Cl]

A target compound was obtained with the yield of 12% by the same synthesis process as described in Example 1 except that 3,5-dichlorobenzeneamine was used instead of 4-chlorobenzeneamine.

$^1$H NMR (CD$_3$CD, 300 MHz) δ 8.06 (s, 1H), 7.64 (s, 2H), 7.29 (s, 2H), 3.66 (t, J=6.55 Hz, 2H), 3.00 (t, J=8.00 Hz, 2H), 2.04 (m, 2H);

Mass (M+H$^+$) calcd for C$_{13}$H$_{14}$C$_{13}$N$_5$ 345.0, found 346.0.

Example 3: Preparation of N4-(3-aminopropyl)-5-chloro-N2-(4-isopropylphenyl)pyrimidine-2,4-diamine

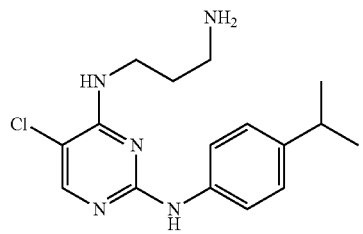 [SMILES: CC(C)c1ccc(Nc2ncc(Cl)c(NCCCN)n2)cc1]

A target compound was obtained with the yield of 21% by the same synthesis process as described in Example 1 except that 4-isopropylbenzeneamine was used instead of 4-chlorobenzeneamine.

$^1$H NMR (CD$_3$CD, 300 MHz) δ 7.94 (s, 1H), 7.43 (d, J=8.46 Hz, 2H), 7.33 (d, J=8.46 Hz, 2H), 3.65 (t, J=6.57 Hz, 2H), 2.93 (m, 3H), 2.02 (m, 2H), 1.28 (d, J=6.90 Hz, 6H);
Mass (M+H$^+$) calcd for C$_{16}$H$_{22}$ClN$_5$ 319.1, found 320.0.

Example 4: Preparation of N4-(3-aminopropyl)-5-chloro-N2-(4-pentylphenyl)pyrimidine-2,4-diamine

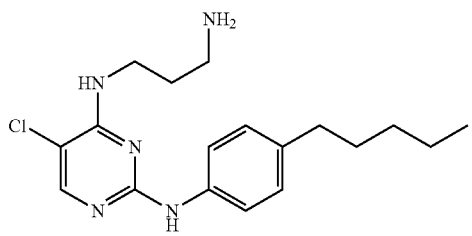 [SMILES: CCCCCc1ccc(Nc2ncc(Cl)c(NCCCN)n2)cc1]

A target compound was obtained with the yield of 26% by the same synthesis process as described in Example 1 except that 4-pentylbenzeneamine was used instead of 4-chlorobenzeneamine.

$^1$H NMR (CD$_3$CD, 300 MHz) δ 7.92 (s, 1H), 7.43 (d, J=8.28 Hz, 2H), 7.24 (d, J=8.25 Hz, 2H), 3.64 (t, J=6.48 Hz, 2H), 2.97 (t, J=7.53 Hz, 2H), 2.63 (t, J=7.53 Hz, 2H), 2.01 (m, 2H), 1.63 (m, 2H), 1.36 (m, 4H), 0.92 (t, J=6.57 Hz, 3H);
Mass (M+H$^+$) calcd for C$_{18}$H$_{26}$ClN$_5$ 347.1, found 348.1.

Example 5: Preparation of N4-(3-aminopropyl)-5-chloro-N2-(4-octylphenyl)pyrimidine-2,4-diamine

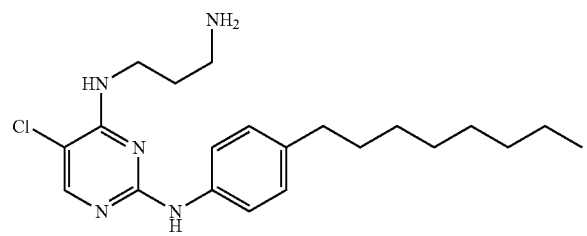 [SMILES: CCCCCCCCc1ccc(Nc2ncc(Cl)c(NCCCN)n2)cc1]

A target compound was obtained with the yield of 49% by the same synthesis process as described in Example 1 except that 4-octylbenzeneamine was used instead of 4-chlorobenzeneamine.

$^1$H NMR (CD$_3$CD, 300 MHz) δ 7.87 (s, 1H), 7.36 (d, J=8.40 Hz, 2H), 7.21 (d, J=8.40 Hz, 2H), 3.59 (t, J=6.57 Hz, 2H), 2.91 (t, J=7.68 Hz, 2H), 2.58 (t, J=8.28 Hz, 2H), 1.93 (m, 2H), 1.58 (m, 2H), 1.25 (m, 8H), 0.85 (t, J=6.99 Hz, 3H);
Mass (M+H$^+$) calcd for C$_{21}$H$_{32}$ClN$_5$ 389.2, found 390.2.

Example 6: Preparation of N4-(3-aminopropyl)-5-chloro-N2-(3-chloro-4-methylphenyl)pyrimidine-2,4-diamine

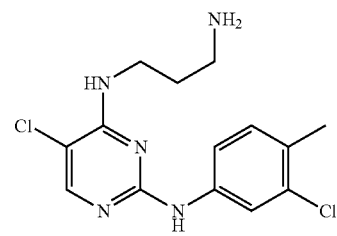

A target compound was obtained with the yield of 38% by the same synthesis process as described in Example 1 except that 3-chloro-4-methylbenzeneamine was used instead of 4-chlorobenzeneamine.

$^1$H NMR (CD$_3$CD, 300 MHz) δ 7.96 (s, 1H), 7.83 (s, 1H), 7.28 (m, 2H), 3.65 (t, J=6.60 Hz, 2H), 3.01 (t, J=7.68 Hz, 2H), 2.35 (s, 3H), 2.02 (m, 2H);
Mass (M+H$^+$) calcd for C$_{14}$H$_{17}$C$_{12}$N$_5$ 325.1, found 326.1.

Example 7: Preparation of N4-(3-aminopropyl)-5-chloro-N2-(3-chloro-4-fluorophenyl)pyrimidine-2,4-diamine

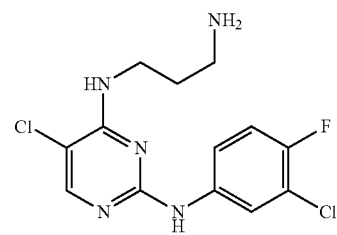

A target compound was obtained with the yield of 11% by the same synthesis process as described in Example 1 except that 3-chloro-4-fluorobenzeneamine was used instead of 4-chlorobenzeneamine.

$^1$H NMR (CD$_3$CD, 300 MHz) δ 8.04 (dd, J=6.72 Hz, 2.64 Hz, 1H), 7.90 (s, 1H), 7.40 (m, 1H), 7.15 (m 1H), 3.62 (t, J=6.42 Hz, 2H), 3.01 (t, J=7.47 Hz, 2H), 2.03 (m, 2H);
Mass (M+H$^+$) calcd for C$_{13}$H$_{14}$C$_{12}$FN$_5$ 329.0, found 330.0.

Example 8: Preparation of N4-(3-aminopropyl)-5-chloro-N2-(3,4-dichlorophenyl)pyrimidine-2,4-diamine

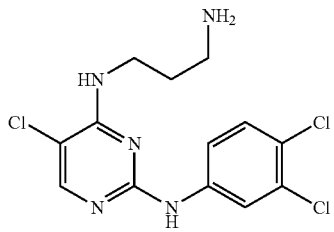 [SMILES: NCCCNc1nc(Nc2ccc(Cl)c(Cl)c2)ncc1Cl]

A target compound was obtained with the yield of 20% by the same synthesis process as described in Example 1 except that 3,4-dichlorobenzeneamine was used instead of 4-chlorobenzeneamine.

$^1$H NMR (CD$_3$CD, 300 MHz) δ 8.11 (s, 1H), 7.98 (s, 1H), 7.43 (m, 2H), 3.65 (t, J=6.57 Hz, 2H), 2.99 (t, J=8.01 Hz, 2H), 2.02 (m, 2H);

Mass (M+H$^+$) calcd for C$_{13}$H$_{14}$Cl$_3$N$_5$ 345.0, found 346.0.

Example 9: Preparation of N4-(3-aminopropyl)-5-chloro-N2-(4-fluorophenyl)pyrimidine-2,4-diamine

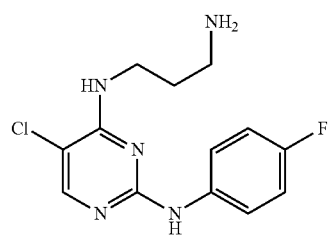 [SMILES: NCCCNc1nc(Nc2ccc(F)cc2)ncc1Cl]

A target compound was obtained with the yield of 40% by the same synthesis process as described in Example 1 except that 4-fluorobenzeneamine was used instead of 4-chlorobenzeneamine.

$^1$H NMR (CD$_3$CD, 500 MHz) δ 7.99 (s, 1H), 7.53 (m, 2H), 7.24 (t, J=8.60 Hz, 2H), 3.64 (t, J=6.60 Hz, 2H), 2.96 (t, J=7.70 Hz, 2H), 2.01 (m, 2H);

Mass (M+H$^+$) calcd for C$_{13}$H$_{15}$ClFN$_5$ 295.1, found 296.1.

Example 10: Preparation of N4-(3-aminopropyl)-5-chloro-N2-(4-phenoxyphenyl)pyrimidine-2,4-diamine

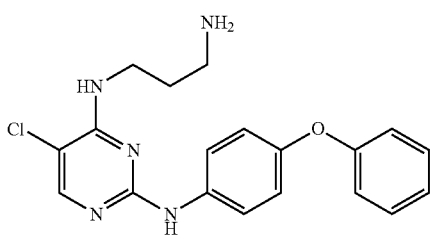 [SMILES: NCCCNc1nc(Nc2ccc(Oc3ccccc3)cc2)ncc1Cl]

A target compound was obtained with the yield of 89% by the same synthesis process as described in Example 1 except that 4-phenoxybenzeneamine was used instead of 4-chlorobenzeneamine.

$^1$H NMR (CD$_3$CD, 500 MHz) δ 7.96 (s, 1H), 7.48 (d, J=8.75 Hz, 2H), 7.41 (m, 2H), 7.17 (t, J=7.5 Hz, 1H), 7.10 (m, 2H), 7.05 (d, J=7.90 Hz, 2H), 3.66 (t, J=6.65 Hz, 2H), 2.98 (t, J=7.70 Hz, 2H), 2.02 (m, 2H);

Mass (M+H$^+$) calcd for C$_{19}$H$_{20}$ClN$_5$O 369.1, found 370.1.

Example 11: Preparation of N4-(3-aminopropyl)-5-chloro-N2-(4-ethylphenyl)pyrimidine-2,4-diamine

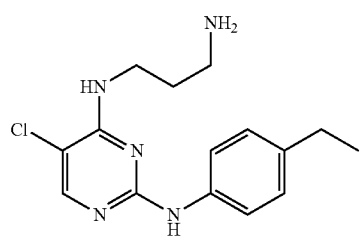 [SMILES: CCc1ccc(Nc2ncc(Cl)c(NCCCN)n2)cc1]

A target compound was obtained with the yield of 55% by the same synthesis process as described in Example 1 except that 4-ethylbenzeneamine was used instead of 4-chlorobenzeneamine.

$^1$H NMR (CD$_3$CD, 500 MHz) δ 7.94 (s, 1H), 7.40 (d, J=8.25 Hz, 2H), 7.33 (d, J=8.35 Hz, 2H), 3.66 (t, J=6.70 Hz, 2H), 2.98 (t, J=7.75 Hz, 2H), 2.70 (m, 2H), 2.02 (m, 2H), 1.27 (t, J=7.60 Hz, 3H);

Mass (M+H$^+$) calcd for C$_{15}$H$_{20}$ClN$_5$ 305.1, found 305.9.

Example 12: Preparation of N4-(3-aminopropyl)-5-chloro-N2-(4-hexylphenyl)pyrimidine-2,4-diamine

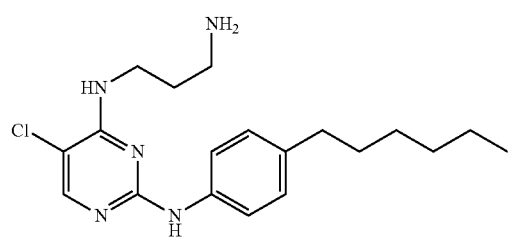 [SMILES: CCCCCCc1ccc(Nc2ncc(Cl)c(NCCCN)n2)cc1]

A target compound was obtained with the yield of 20% by the same synthesis process as described in Example 1 except that 4-hexylbenzeneamine was used instead of 4-chlorobenzeneamine.

$^1$H NMR (CD$_3$CD, 500 MHz) δ 7.94 (s, 1H), 7.39 (d, J=8.15 Hz, 2H), 7.31 (d, J=8.25 Hz, 2H), 3.66 (t, J=6.50 Hz, 2H), 2.99 (t, J=7.60 Hz, 2H), 2.67 (t, J=7.60 Hz, 2H), 2.04 (m, 2H), 1.64 (m, 2H), 1.36 (m, 6H), 0.92 (t, J=6.80 Hz, 3H);

Mass (M+H$^+$) calcd for C$_{19}$H$_{28}$ClN$_5$ 361.2, found 362.2.

Example 13: Preparation of N4-(3-aminopropyl)-5-chloro-N2-(4-(4-nitrophenylsulfonyl)phenyl)pyrimidine-2,4-diamine

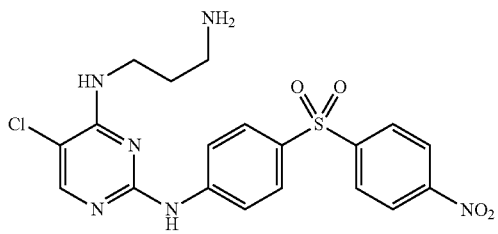 [SMILES: NCCCNc1nc(Nc2ccc(S(=O)(=O)c3ccc([N+](=O)[O-])cc3)cc2)ncc1Cl]

A target compound was obtained with the yield of 30% by the same synthesis process as described in Example 1 except that 4-(4-nitrophenylsulfonyl)benzeneamine was used instead of 4-chlorobenzeneamine.

$^1$H NMR (CD$_3$CD, 500 MHz) δ 8.44 (d, J=8.85 Hz, 2H), 8.25 (d, J=8.80 Hz, 2H), 8.11 (s, 1H), 8.09 (d, J=8.90 Hz, 2H), 7.87 (d, J=8.80 Hz, 2H), 3.70 (t, J=6.70 Hz, 2H), 3.01 (t, J=7.65 Hz, 2H), 2.04 (m, 2H);

Mass (M+H$^+$) calcd for C$_{19}$H$_{19}$ClN$_6$O$_4$S 462.1, found 463.1.

Example 14: Preparation of N4-(3-aminopropyl)-5-chloro-N2-(3,4-dimethylphenyl)pyrimidine-2,4-diamine

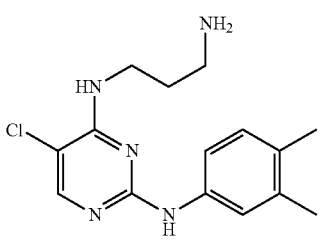 [SMILES: Cc1ccc(Nc2ncc(Cl)c(NCCCN)n2)cc1C]

A target compound was obtained with the yield of 64% by the same synthesis process as described in Example 1 except that 3,4-dimethylbenzeneamine was used instead of 4-chlorobenzeneamine.

$^1$H NMR (CD$_3$CD, 300 MHz) δ 7.91 (s, 1H), 7.21 (m, 3H), 3.66 (t, J=6.42 Hz, 2H), 2.98 (t, J=7.71 Hz, 2H), 2.30 (s, 3H), 2.28 (s, 3H), 2.02 (m, 2H);

Mass (M+H$^+$) calcd for C$_{15}$H$_{20}$ClN$_5$ 305.1, found 306.1.

Example 15: Preparation of N4-(3-aminopropyl)-5-chloro-N2-(4-fluoro-3-(trifluoromethyl)phenyl)pyrimidine-2,4-diamine

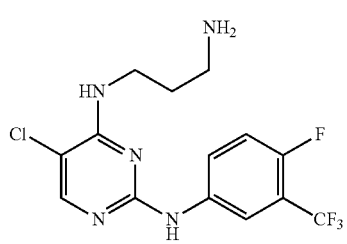 [SMILES: NCCCNc1nc(Nc2ccc(F)c(C(F)(F)F)c2)ncc1Cl]

A target compound was obtained with the yield of 70% by the same synthesis process as described in Example 1 except that 4-fluoro-3-(trifluoromethyl)benzeneamine was used instead of 4-chlorobenzeneamine.

$^1$H NMR (CD$_3$CD, 300 MHz) δ 8.07 (s, 1H), 8.05 (m, 1H), 7.80 (m, 1H), 7.46 (m, 1H), 3.65 (t, J=6.63 Hz, 2H), 2.96 (t, J=7.80 Hz, 2H), 2.00 (m, 2H);

Mass (M+H$^+$) calcd for C$_{14}$H$_{14}$ClF$_4$N$_5$ 363.1, found 364.1.

Example 16: Preparation of N4-(3-aminopropyl)-N2-(4-bromo-3-(trifluoromethyl)phenyl)-5-chloro-pyrimidine-2,4-diamine

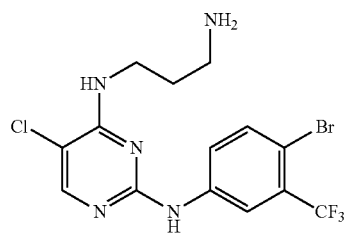

A target compound was obtained with the yield of 18% by the same synthesis process as described in Example 1 except that 4-bromo-3-(trifluoromethyl)benzeneamine was used instead of 4-chlorobenzeneamine.

$^1$H NMR (CD$_3$CD, 300 MHz) δ 8.35 (s, 1H), 7.98 (s, 1H), 7.69 (m, 2H), 3.65 (t, J=6.42 Hz, 2H), 2.99 (t, J=7.65 Hz, 2H), 2.02 (m, 2H);

Mass (M+H$^+$) calcd for C$_{14}$H$_{14}$BrClF$_3$N$_5$ 423.0, found 424.0.

Example 17: Preparation of N4-(3-aminopropyl)-N2-(4-bromophenyl)-5-chloropyrimidine-2,4-diamine

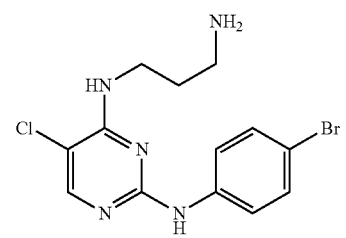 [SMILES: NCCCNc1nc(Nc2ccc(Br)cc2)ncc1Cl]

A target compound was obtained with the yield of 35% by the same synthesis process as described in Example 1 except that 4-bromobenzeneamine was used instead of 4-chlorobenzeneamine.

$^1$H NMR (CD$_3$CD, 300 MHz) δ 7.99 (s, 1H), 7.54 (m, 4H), 3.64 (t, J=6.70 Hz, 2H), 2.98 (t, J=6.57 Hz, 2H), 2.97 (t, J=7.68 Hz, 2H), 1.99 (m, 2H);

Mass (M+H$^+$) calcd for C$_{13}$H$_{15}$BrClN$_5$ 355.0, found 356.0.

Example 18: Preparation of N4-(3-aminopropyl)-5-chloro-N2-(3-chloro-4-methoxyphenyl)pyrimidine-2,4-diamine

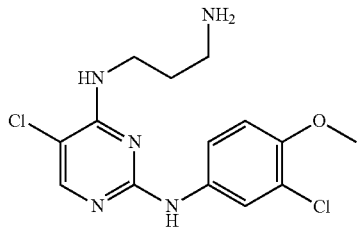 [SMILES: COc1ccc(Nc2ncc(Cl)c(NCCCN)n2)cc1Cl]

A target compound was obtained with the yield of 42% by the same synthesis process as described in Example 1 except that 3-chloro-4-methoxybenzeneamine was used instead of 4-chlorobenzeneamine.

$^1$H NMR (CD$_3$CD, 300 MHz) δ 7.97 (s, 1H), 7.72 (d, J=2.19 Hz, 1H), 7.34 (dd, J=8.85 Hz, 2.55 Hz, 1H), 7.15 (d, J=8.88 Hz, 1H), 3.92 (s, 3H), 3.64 (t, J=6.72 Hz, 2H), 2.98 (t, J=7.80 Hz, 2H), 2.00 (m, 2H);

Mass (M+H$^+$) calcd for C$_{14}$H$_{17}$C$_{12}$N$_5$O 341.1, found 342.1.

Example 19: Preparation of N4-(3-aminopropyl)-N2-(4-chlorophenyl)-5-methylpyrimidine-2,4-diamine

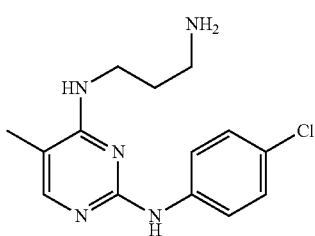 [SMILES: Cc1cnc(Nc2ccc(Cl)cc2)nc1NCCCN]

A target compound was obtained with the yield of 45% by the same synthesis process as described in Example 1 except that 2,4-dichloro-5-methylpyrimidine was used instead of 2,4,5-trichloropyrimidine.

$^1$H NMR (CD$_3$CD, 300 MHz) δ 7.58 (s, 1H), 7.59 (m, 4H), 3.65 (t, J=6.12 Hz, 2H), 2.98 (t, J=7.38 Hz, 2H), 2.09 (s, 3H), 2.02 (m, 2H);

Mass (M+H$^+$) calcd for C$_{14}$H$_{18}$ClN$_5$ 291.1, found 292.0.

Example 20: Preparation of N4-(3-aminopropyl)-N2-(benzo[d][1,3]dioxol-5-yl)-5-chloropyrimidine-2,4-diamine

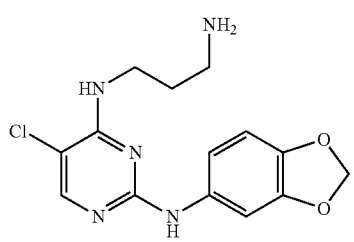

A target compound was obtained with the yield of 21% by the same synthesis process as described in Example 1 except that benzo[d][1,3]dioxol-5-amine was used instead of 4-chlorobenzeneamine.

$^1$H NMR (DMSO-d6, 500 MHz) δ 10.64 (br s, 1H), 8.02 (s, 1H), 7.94 (br s, 1H), 7.38 (s, 2H), 7.01 (d, J=8.44 Hz, 1H), 6.87 (dd, J=8.35 Hz, 1.65 Hz, 2H), 5.99 (s, 2H), 3.47 (m, 2H), 2.80 (m, 2H), 1.88 (m, 2H);

Mass (M+H$^+$) calcd for C$_{14}$H$_{16}$ClN$_5$O$_2$ 321.1, found 322.0.

Example 21: Preparation of N4-(3-aminopropyl)-5-chloro-N2-(2,3-dihydro-1H-indene-5-yl)pyrimidine-2,4-diamine

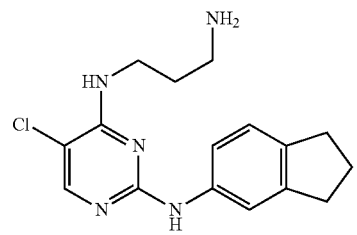

A target compound was obtained with the yield of 34% by the same synthesis process as described in Example 1 except that 2,3-dihydro-1H-indene-5-amine was used instead of 4-chlorobenzeneamine.

$^1$H NMR (DMSO-d6, 300 MHz) δ 9.02 (s, 1H), 7.88 (s, 1H), 7.68 (s, 1H), 7.36 (m, 2H), 7.07 (d, J=8.10 Hz, 1H), 3.46 (m, 2H), 2.80 (m, 4H), 2.62 (m, 2H), 1.99 (m, 2H), 1.65 (m, 2H);

Mass (M+H$^+$) calcd for C$_{16}$H$_{20}$ClN$_5$ 317.14, found 318.1.

Example 22: Preparation of N4-(3-aminopropyl)-5-chloro-N2-(2,3-dihydrobenzo[b][1,4]dioxin-6-yl)pyrimidine-2,4-diamine

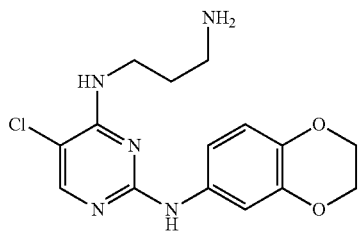 [SMILES: NCCCNc1nc(Nc2ccc3c(c2)OCCO3)ncc1Cl]

A target compound was obtained with the yield of 25% by the same synthesis process as described in Example 1 except that 2,3-dihydrobenzo[b][1,4]dioxin-6-amine was used instead of 4-chlorobenzeneamine.

$^1$H NMR (DMSO-d6, 300 MHz) δ 10.59 (br s, 1H), 8.87 (br s, 1H), 8.20 (s, 1H), 8.15 (br s, 2H), 7.20 (d, J=1.71 Hz, 1H), 6.91 (m, 2H), 4.25 (m, 4H), 3.50 (m, 2H), 2.81 (m, 2H), 1.91 (m, 2H);

Mass (M+H$^+$) calcd for C$_{15}$H$_{18}$ClN$_5$O$_2$ 335.11, found 336.1.

Example 23: Preparation of N4-(3-aminopropyl)-5-chloro-N2-(5,6,7,8-tetrahydronaphthalene-2-yl)pyrimidine-2,4-diamine

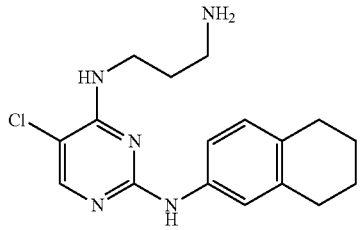

A target compound was obtained with the yield of 30% by the same synthesis process as described in Example 1 except that 5,6,7,8-tetrahydronaphthalene-2-amine was used instead of 4-chlorobenzeneamine.

$^1$H NMR (DMSO-d6, 300 MHz) δ 10.14 (br s, 1H), 8.41 (br s, 1H), 8.14 (s, 1H), 8.05 (br s, 2H), 7.37 (s, 1H), 7.28 (d, J=7.35 Hz, 1H), 7.02 (d, J=7.89 Hz, 1H), 3.51 (m, 2H), 2.81 (m, 2H), 2.70 (m, 4H), 1.91 (m, 2H), 1.73 (m, 4H);

Mass (M+H$^+$) calcd for $C_{17}H_{22}ClN_5$ 331.1, found 331.9.

Example 24: Preparation of 6-(4-(3-aminopropylamino)-5-chloropyrimidine-2-ylamino)-3,4-dihydronaphthalene-1(2H)-one

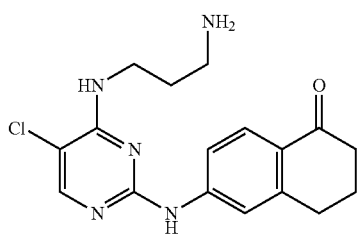 [SMILES: NCCCNc1nc(Nc2ccc3c(c2)CCCC3=O)ncc1Cl]

A target compound was obtained with the yield of 20% by the same synthesis process as described in Example 1 except that 6-amino-3,4-dihydronaphthalene-1(2H)-one was used instead of 4-chlorobenzeneamine.

$^1$H NMR (CD$_3$CD, 500 MHz) δ 8.10 (s, 1H), 8.04 (d, J=8.55 Hz, 1H), 7.60 (d, J=8.55 Hz, 1H), 7.54 (br s, 1H), 3.72 (t, J=6.60 Hz, 2H), 3.04 (m, 4H), 2.68 (t, J=6.30 Hz, 2H), 2.17 (m, 2H), 2.08 (m, 2H);

Mass (M+H$^+$) calcd for $C_{17}H_{20}ClN_5O$ 345.14, found 346.1.

Example 25: Preparation of N4-(3-aminopropyl)-5-chloro-N2-(4-(piperazine-1-yl)phenyl)pyrimidine-2,4-diamine

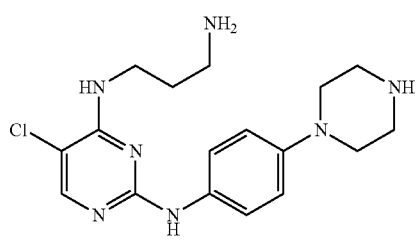

A target compound was obtained with the yield of 30% by the same synthesis process as described in Example 1 except that 4-(piperazine-1-yl)benzeneamine was used instead of 4-chlorobenzeneamine.

$^1$H NMR (DMSO-d6, 300 MHz) δ 10.64 (br s, 1H), 9.41 (br s, 1H), 8.92 (br s, 1H), 8.22 (s, 1H), 8.16 (br s, 2H), 7.45 (d, J=8.82 Hz, 2H), 7.08 (d, J=8.80 Hz, 2H), 3.51 (m, 2H), 3.39 (br s, 4H), 3.21 (br s, 4H), 2.77 (m, 2H), 1.88 (m, 2H);

Mass (M+H$^+$) calcd for $C_{17}H_{24}ClN_7$ 361.1, found 361.8.

Example 26: Preparation of N4-(3-aminopropyl)-5-chloro-N2-(4-(piperidine-4-yl)phenyl)pyrimidine-2,4-diamine

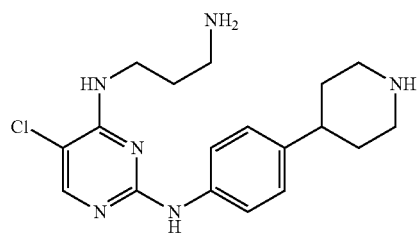 [SMILES: NCCCNc1nc(Nc2ccc(C3CCNCC3)cc2)ncc1Cl]

A target compound was obtained with the yield of 15% by the same synthesis process as described in Example 1 except that 4-(piperidine-4-yl)benzeneamine was used instead of 4-chlorobenzeneamine.

$^1$H NMR (CD$_3$CD, 300 MHz) δ 7.97 (s, 1H), 7.51 (d, J=8.43 Hz, 2H), 7.38 (d, J=8.52 Hz, 2H), 3.66 (t, J=6.63 Hz, 2H), 3.53 (m, 2H), 3.16 (m, 2H), 2.98 (t, J=7.41 Hz, 2H), 2.00 (m, 6H);

Mass (M+H$^+$) calcd for $C_{18}H_{25}ClN_6$ 360.1, found 361.1.

Example 27: Preparation of N4-(3-aminopropyl)-N2-(3-chloro-4-methylphenyl)-5-methylpyrimidine-2,4-diamine

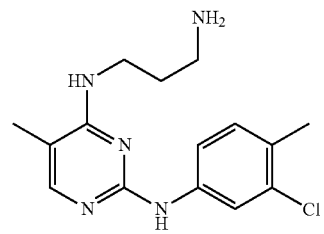

A target compound was obtained with the yield of 27% by the same synthesis process as described in Example 1 except that 2,4-dichloro-5-methylpyrimidine was used instead of 2,4,5-trichloropyrimidine and 3-chloro-4-methylbenzeneamine was used instead of 4-chlorobenzeneamine.

$^1$H NMR (CD$_3$CD, 300 MHz) δ 7.80 (s, 1H), 7.56 (s, 1H), 7.30 (br s, 2H), 3.66 (t, J=6.57 Hz, 2H), 3.02 (t, J=7.62 Hz, 2H), 2.33 (s, 3H), 2.06 (br s, 5H);

Mass (M+H$^+$) calcd for $C_{15}H_{20}ClN_5$ 305.1, found 306.1.

Example 28: Preparation of N4-(3-aminopropyl)-N2-(4-fluorophenyl)-5-methylpyrimidine-2,4-diamine

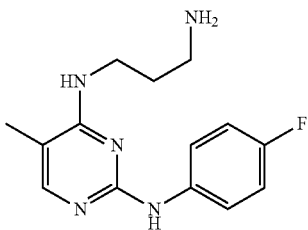 [SMILES: Cc1cnc(Nc2ccc(F)cc2)nc1NCCCN]

A target compound was obtained with the yield of 49% by the same synthesis process as described in Example 1 except that 2,4-dichloro-5-methylpyrimidine was used instead of 2,4,5-trichloropyrimidine and 4-fluorobenzeneamine was used instead of 4-chlorobenzeneamine.

$^1$H NMR (CD$_3$CD, 300 MHz) δ 7.54 (s, 1H), 7.52 (m, 2H), 7.18 (m, 2H), 3.63 (t, J=6.54 Hz, 2H), 2.95 (t, J=7.65 Hz, 2H), 2.06 (s, 3H), 2.00 (m, 2H);

Mass (M+H$^+$) calcd for C$_{14}$H$_{18}$FN$_5$ 275.1, found 276.0.

Example 29: Preparation of N4-(3-aminopropyl)-5-methyl-N2-(4-(piperazine-1-yl)phenyl)pyrimidine-2,4-diamine

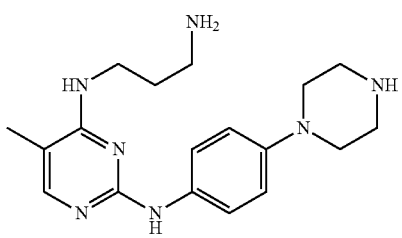 [SMILES: Cc1cnc(Nc2ccc(N3CCNCC3)cc2)nc1NCCCN]

A target compound was obtained with the yield of 4% by the same synthesis process as described in Example 1 except that 2,4-dichloro-5-methylpyrimidine was used instead of 2,4,5-trichloropyrimidine and 4-(piperazine-1-yl)benzeneamine was used instead of 4-chlorobenzeneamine.

$^1$H NMR (CD3CD, 500 MHz) δ 7.48 (s, 1H), 7.39 (d, J=8.65 Hz, 2H), 7.14 (d, J=8.75 Hz, 2H), 3.65 (t, J=6.50 Hz, 2H), 3.44 (m, 8H), 2.99 (t, J=7.50 Hz, 2H), 2.06 (br s, 5H);

Mass (M+H$^+$) calcd for C$_{18}$H$_{27}$N$_7$ 341.2, found 342.1.

Example 30: Preparation of N4-(3-aminopropyl)-5-methyl-N2-(5,6,7,8-tetrahydronaphthalene-2-yl)pyrimidine-2,4-diamine

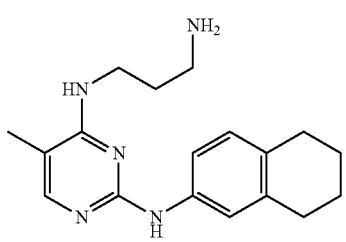 [SMILES: Cc1cnc(Nc2ccc3c(c2)CCCC3)nc1NCCCN]

A target compound was obtained with the yield of 31% by the same synthesis process as described in Example 1 except that 2,4-dichloro-5-methylpyrimidine was used instead of 2,4,5-trichloropyrimidine and 5,6,7,8-tetrahydronaphthalene-2-amine was used instead of 4-chlorobenzeneamine.

$^1$H NMR (CD$_3$CD, 300 MHz) δ 7.48 (s, 1H), 7.17 (m, 3H), 3.65 (t, J=6.57 Hz, 2H), 2.98 (t, J=7.59 Hz, 2H), 2.79 (br s, 4H), 2.05 (br s, 5H), 1.83 (br s, 4H);

Mass (M+H$^+$) calcd for C$_{18}$H$_{25}$N$_5$ 311.2, found 312.1.

Example 31: Preparation of N4-(3-aminopropyl)-N2-(4-fluoro-3-(trifluoromethyl)phenyl)-5-methylpyrimidine-2,4-diamine

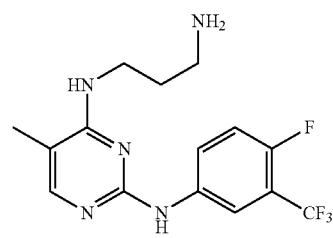 [SMILES: Cc1cnc(Nc2ccc(F)c(C(F)(F)F)c2)nc1NCCCN]

A target compound was obtained with the yield of 3% by the same synthesis process as described in Example 1 except that 2,4-dichloro-5-methylpyrimidine was used instead of 2,4,5-trichloropyrimidine and 4-fluoro-3-(trifluoromethyl)benzeneamine was used instead of 4-chlorobenzeneamine.

$^1$H NMR (CD$_3$CD, 300 MHz) δ 8.23 (m, 1H), 7.71 (m, 1H), 7.68 (s, 1H), 7.23 (t, J=9.72 Hz, 1H), 3.63 (t, J=6.09 Hz, 2H), 2.98 (t, J=7.32 Hz, 2H), 2.00 (br s, 5H);

Mass (M+H$^+$) calcd for C$_{15}$H$_{17}$F$_4$N$_5$ 343.1, found 344.0.

Example 32: Preparation of N4-(3-aminopropyl)-N2-(4-bromo-3-(trifluoromethyl)phenyl)-5-methylpyrimidine-2,4-diamine

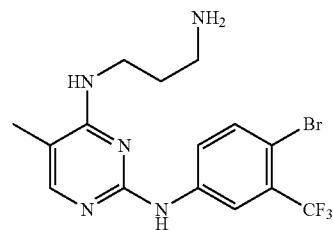 [SMILES: Cc1cnc(Nc2ccc(Br)c(C(F)(F)F)c2)nc1NCCCN]

A target compound was obtained with the yield of 2% by the same synthesis process as described in Example 1 except that 2,4-dichloro-5-methylpyrimidine was used instead of 2,4,5-trichloropyrimidine and 4-bromo-3-(trifluoromethyl)benzeneamine was used instead of 4-chlorobenzeneamine.

$^1$H NMR (CD$_3$CD, 300 MHz) δ 8.39 (s, 1H), 7.71 (s, 1H), 7.66 (br s, 2H), 3.64 (t, J=6.06 Hz, 2H), 2.99 (t, J=7.44 Hz, 2H), 2.01 (br s, 5H);

Mass (M+H$^+$) calcd for C$_{15}$H$_{17}$BrF$_3$N$_5$ 403.0, found 403.9.

Example 33: Preparation of N4-(3-aminopropyl)-5-methyl-N2-(4-phenoxyphenyl)pyrimidine-2,4-diamine

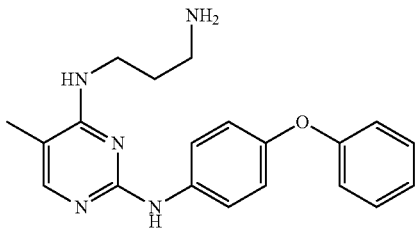 [SMILES: Cc1cnc(Nc2ccc(Oc3ccccc3)cc2)nc1NCCCN]

A target compound was obtained with the yield of 3% by the same synthesis process as described in Example 1 except that 2,4-dichloro-5-methylpyrimidine was used instead of 2,4,5-trichloropyrimidine and 4-phenoxybenzeneamine was used instead of 4-chlorobenzeneamine.

$^1$H NMR (CD$_3$CD, 300 MHz) δ 7.57 (s, 1H), 7.50 (d, J=8.75 Hz, 2H), 7.37 (m, 2H), 7.13 (t, J=7.44 Hz, 1H), 7.03 (m, 4H), 3.63 (m, 2H), 2.96 (t, J=7.44 Hz, 2H), 2.04 (m, 5H);

Mass (M+H$^+$) calcd for C$_{20}$H$_{23}$N$_5$O 349.1, found 350.1.

Example 34: Preparation of N4-(3-aminopropyl)-5-methyl-N2-(4-(4-nitrophenylsulfonyl)phenyl)pyrimidine-2,4-diamine

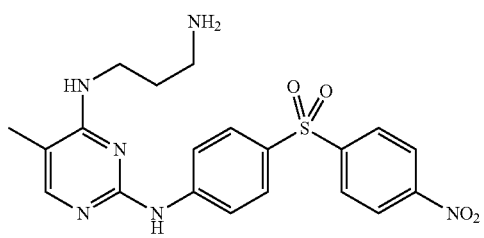 [SMILES: Cc1cnc(Nc2ccc(S(=O)(=O)c3ccc([N+](=O)[O-])cc3)cc2)nc1NCCCN]

A target compound was obtained with the yield of 3% by the same synthesis process as described in Example 1 except that 2,4-dichloro-5-methylpyrimidine was used instead of 2,4,5-trichloropyrimidine and 4-(4-nitrophenylsulfonyl)benzeneamine was used instead of 4-chlorobenzeneamine.

$^1$H NMR (CD3CD, 300 MHz) δ 8.41 (d, J=8.88 Hz, 2H), 8.19 (d, J=8.88 Hz, 2H), 7.91 (m, 4H), 7.73 (s, 1H), 3.68 (m, 2H), 3.00 (t, J=7.29 Hz, 2H), 1.98 (br s, 5H);

Mass (M–H$^-$) calcd for C$_{20}$H$_{22}$N$_6$O$_4$S 442.1, found 440.9.

Example 35: Preparation of N4-(3-aminopropyl)-N2-(4-bromophenyl)-5-methylpyrimidine-2,4-diamine

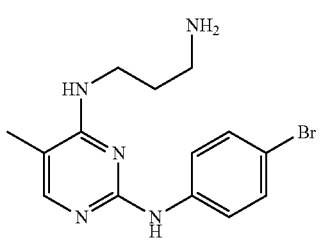 [SMILES: Cc1cnc(Nc2ccc(Br)cc2)nc1NCCCN]

A target compound was obtained with the yield of 8% by the same synthesis process as described in Example 1 except that 2,4-dichloro-5-methylpyrimidine was used instead of 2,4,5-trichloropyrimidine and 4-bromobenzeneamine was used instead of 4-chlorobenzeneamine.

$^1$H NMR (CD$_3$CD, 300 MHz) δ 7.53 (m, 5H), 3.64 (t, J=6.15 Hz, 2H), 2.97 (t, J=7.17 Hz, 2H), 2.01 (m, 5H);

Mass (M+M$^+$) calcd for C$_{14}$H$_{18}$BrN$_5$ 335.1, found 336.0.

Example 36: Preparation of N4-(3-aminopropyl)-N2-(2,3-dihydrobenzo[b][1,4]dioxin-6-yl)-5-methylpyrimidine-2,4-diamine

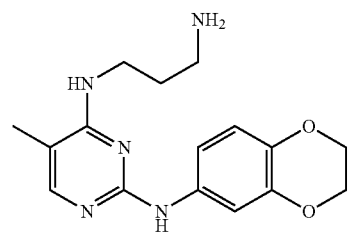 [SMILES: Cc1cnc(Nc2ccc3c(c2)OCCO3)nc1NCCCN]

A target compound was obtained with the yield of 35% by the same synthesis process as described in Example 1 except that 2,4-dichloro-5-methylpyrimidine was used instead of 2,4,5-trichloropyrimidine and 2,3-dihydrobenzo[b][1,4]dioxin-6-amine was used instead of 4-chlorobenzeneamine.

$^1$H NMR (CD$_3$CD, 300 MHz) δ 7.48 (s, 1H), 7.14 (br s, 1H), 6.87 (br s, 2H), 4.27 (br s, 4H), 3.63 (t, J=6.69 Hz, 2H), 3.01 (t, J=8.53 Hz, 2H), 2.05 (br s, 5H);

Mass (M+H$^+$) calcd for C$_{16}$H$_{21}$N$_5$O$_2$ 315.1, found 316.1.

Example 37: Preparation of N4-(3-aminopropyl)-N2-(3,4-dimethylphenyl)-5-methylpyrimidine-2,4-diamine

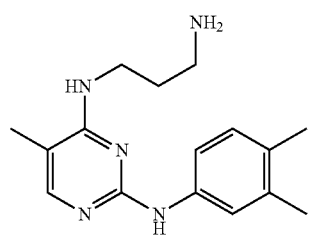

A target compound was obtained with the yield of 36% by the same synthesis process as described in Example 1 except that 2,4-dichloro-5-methylpyrimidine was used instead of 2,4,5-trichloropyrimidine and 3,4-dimethylbenzeneamine was used instead of 4-chlorobenzeneamine.

$^1$H NMR (CD$_3$CD, 300 MHz) δ 7.48 (s, 1H), 7.25 (s, 1H), 7.20 (br s, 2H), 3.65 (t, J=6.48 Hz, 2H), 2.97 (t, J=7.68 Hz, 2H), 2.30 (s, 3H), 2.28 (s, 3H), 2.05 (br s, 5H);

Mass (M+H$^+$) calcd for C$_{16}$H$_{23}$N$_5$ 285.2, found 286.1.

Example 38: Preparation of N4-(3-aminopropyl)-N2-(3-chloro-4-fluorophenyl)-5-methylpyrimidine-2,4-diamine

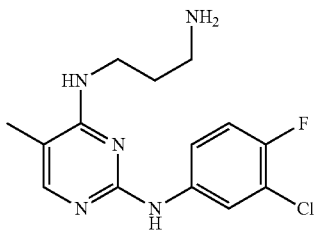

A target compound was obtained with the yield of 26% by the same synthesis process as described in Example 1 except that 2,4-dichloro-5-methylpyrimidine was used instead of 2,4,5-trichloropyrimidine and 3-chloro-4-fluorobenzeneamine was used instead of 4-chlorobenzeneamine.

$^1$H NMR (CD$_3$CD, 300 MHz) δ 7.89 (m, 1H), 7.60 (br s, 1H), 7.43 (m, 1H), 7.30 (m 1H), 3.65 (t, J=6.69 Hz, 2H), 3.00 (t, J=7.68 Hz, 2H), 2.08 (br s, 5H);

Mass (M+H$^+$) calcd for C$_{14}$H$_{17}$ClFN$_5$ 309.1, found 310.0.

Example 39: Preparation of N4-(3-aminopropyl)-N2-(3,4-dichlorophenyl)-5-methylpyrimidine-2,4-diamine

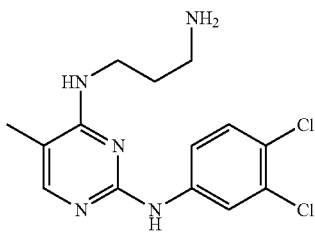 [SMILES: Cc1cnc(Nc2ccc(Cl)c(Cl)c2)nc1NCCCN]

A target compound was obtained with the yield of 26% by the same synthesis process as described in Example 1 except that 2,4-dichloro-5-methylpyrimidine was used instead of 2,4,5-trichloropyrimidine and 3,4-dichlorobenzeneamine was used instead of 4-chlorobenzeneamine.

$^1$H NMR (CD3CD, 300 MHz) δ 8.03 (s, 1H), 7.61 (s, 1H), 7.53 (d, J=8.73 Hz, 1H), 7.41 (dd, J=8.73 Hz, 2.34 Hz, 1H), 3.67 (t, J=6.72 Hz, 2H), 3.03 (t, J=7.62 Hz, 2H), 2.08 (br s, 5H);

Mass (M−H$^-$) calcd for C$_{14}$H$_{17}$C$_{12}$N$_5$ 325.1, found 323.9.

The specific structures of the compounds prepared in Example 1~Example 39 are shown in Table 1 below.

Example 40: Preparation of N4-(4-n-aminobutyl)-N2-(4-chlorophenyl)-5-chloropyrimidine-2,4-diamine

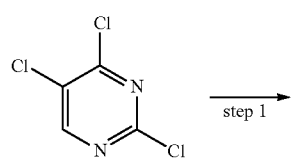

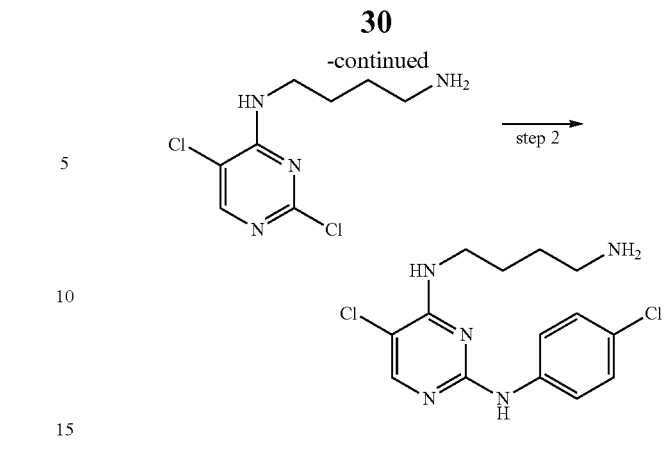

Step 1: Preparation of tert-butyl (4-((2,5-dichloropyrimidine-4-yl)amino)butyl)carbamate A target compound was obtained by the same manner as described in Preparative Example 1, except that tert-butyl (4-aminobutyl)carbamate was used in step 1 (yield: 46%).

$^1$H NMR (CDCl$_3$, 300 MHz) δ 8.00 (s, 1H), 5.65 (br s, 1H), 4.62 (br s, 1H), 3.55 (m, 2H), 3.18 (m, 2H), 1.68 (m, 4H), 1.44 (s, 9H).

Step 2: Preparation of N4-(4-aminobutyl)-5-chloro-N2-(4-chlorophenyl)pyrimidine-2,4-diamine A target compound was obtained by the same manner as described in Preparative Example 1, except that tert-butyl (4-((2,5-dichloropyrimidine-4-yl)amino)butyl)carbamate was used in step 2 (yield: 30%).

$^1$H NMR (DMSO-d$_6$, 300 MHz) δ 10.27 (br s, 1H), 8.26 (br s, 2H), 8.14 (s, 1H), 7.91 (br s, 2H), 7.68 (d, J=8.91 Hz, 2H), 7.41 (d, J=8.85 Hz, 2H), 3.42 (m, 2H), 2.78 (m, 2H), 1.61 (m, 4H);

Mass (M+H$^+$) calcd for C$_{14}$H$_{17}$C$_{12}$N$_5$ 325.1, found 326.1.

Example 41: Preparation of N4-(4-n-aminobutyl)-N2-(3,5-dichlorophenyl)-5-chloropyrimidine-2,4-diamine

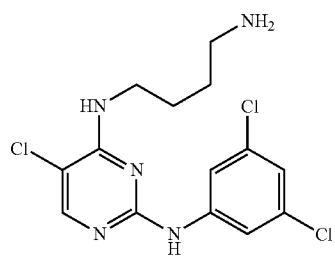 [SMILES: NCCCCNc1nc(Nc2cc(Cl)cc(Cl)c2)ncc1Cl]

A target compound was obtained by the same synthesis process as described in Example 2 except that tert-butyl (3-aminobutyl)carbamate was used instead of tert-butyl (3-aminopropyl)carbamate (yield: 12%).

$^1$H NMR (CD$_3$OD, 300 MHz) δ 7.91 (s, 1H), 7.77 (s, 2H), 6.98 (s, 1H), 3.59 (m, 2H), 2.98 (m, 2H), 1.80 (m, 4H);

Mass (M+H$^+$) calcd for C$_{14}$H$_{16}$C$_{13}$N$_5$ 359.0, found 360.1.

Comparative Example 1: Preparation of N4-(3-aminopropyl)-N2-(4-chlorophenyl)-5-fluoropyrimidine-2,4-diamine

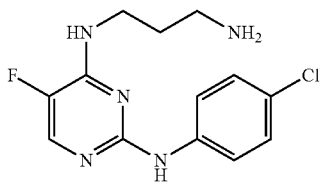 [SMILES: NCCCNc1nc(Nc2ccc(Cl)cc2)ncc1F]

A target compound was obtained by the same synthesis process as described in Example 1 except that 2,4-dichloro-5-fluoropyrimidine was used instead of 2,4,5-trichloropyrimidine.

Comparative Example 2: Preparation of N4-(3-aminopropyl)-N2-(4-chlorophenyl)-5-(trifluoromethyl)pyrimidine-2,4-diamine

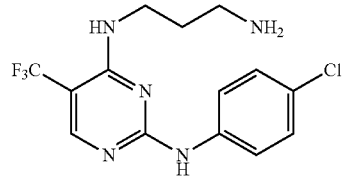 [SMILES: NCCCNc1nc(Nc2ccc(Cl)cc2)ncc1C(F)(F)F]

A target compound was obtained by the same synthesis process as described in Example 1 except that 2,4-dichloro-5-(trifluoromethyl)pyrimidine was used instead of 2,4,5-trichloropyrimidine.

Comparative Example 3: Preparation of N4-(3-aminopropyl)-N2-(4-chlorophenyl)-5-methoxypyrimidine-2,4-diamine

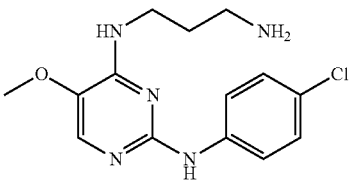 [SMILES: COc1cnc(Nc2ccc(Cl)cc2)nc1NCCCN]

A target compound was obtained by the same synthesis process as described in Example 1 except that 2,4-dichloro-5-methoxypyrimidine was used instead of 2,4,5-trichloropyrimidine.

Comparative Example 4: Preparation of N4-(3-aminopropyl)-N2-(4-chlorophenyl)pyrimidine-2,4-diamine

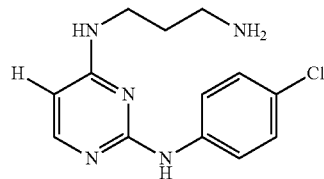

A target compound was obtained by the same synthesis process as described in Example 1 except that 2,4-dichloropyrimidine was used instead of 2,4,5-trichloropyrimidine.

Comparative Example 5: Preparation of N4-(3-aminopropyl)-N2-(4-chlorophenyl)-5-nitropyrimidine-2,4-diamine

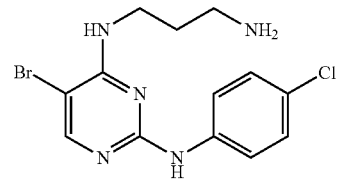

A target compound was obtained by the same synthesis process as described in Example 1 except that 2,4-dichloro-5-nitropyrimidine was used instead of 2,4,5-trichloropyrimidine.

Comparative Example 6: Preparation of N4-3-aminopropyl)-5-bromo-N2-(4-chlorophenyl)pyrimidine-2,4-diamine

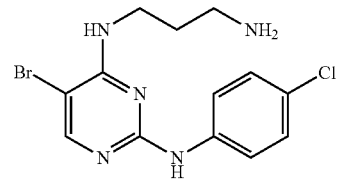

A target compound was obtained by the same synthesis process as described in Example 1 except that 5-bromo-2,4-dichloropyrimidine was used instead of 2,4,5-trichloropyrimidine.

Comparative Example 7: Preparation of N4-(2-aminoethyl)-5-chloro-N2-(4-chlorophenyl)pyrimidine-2,4-diamine

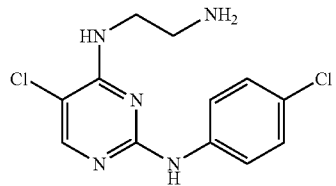 [SMILES: NCCNc1nc(Nc2ccc(Cl)cc2)ncc1Cl]

A target compound was obtained by the same synthesis process as described in Example 1 except that tert-butyl(3-aminoethyl)carbamate was used instead of tert-butyl (3-aminopropyl)carbamate.

Comparative Example 8: Preparation of N4-(2-aminoethyl)-N2-(4-chlorophenyl)-5-methylpyrimidine-2,4-diamine

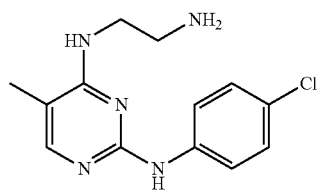 [SMILES: Cc1cnc(Nc2ccc(Cl)cc2)nc1NCCN]

A target compound was obtained by the same synthesis process as described in Example 19 except that tert-butyl (3-aminoethyl)carbamate was used instead of tert-butyl (3-aminopropyl)carbamate.

The specific structures of the compounds prepared in Example 1~Example 41 are shown in Table 1 below, and the specific structures of the compounds prepared in Comparative Example 1~Comparative Example 8 are shown in Table 2 below.

TABLE 1

| Example | Chemical Structure |
|---|---|
| (1) | |
| (2) | |
| (3) | 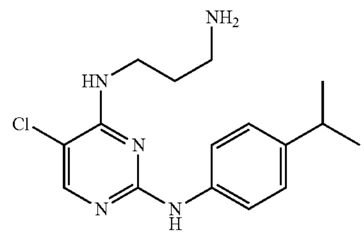 [SMILES: CC(C)c1ccc(Nc2ncc(Cl)c(NCCCN)n2)cc1] |
| (4) | 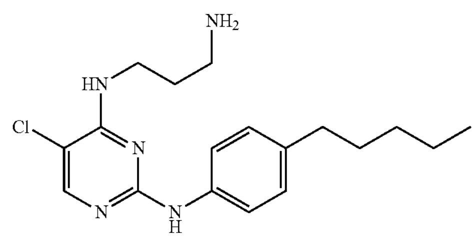 [SMILES: CCCCCc1ccc(Nc2ncc(Cl)c(NCCCN)n2)cc1] |
| (5) | 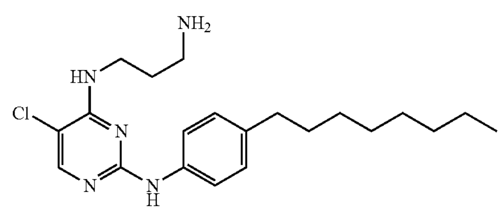 [SMILES: CCCCCCCCc1ccc(Nc2ncc(Cl)c(NCCCN)n2)cc1] |
| (6) | 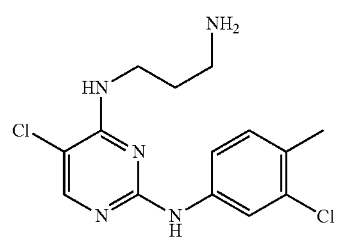 |
| (7) | 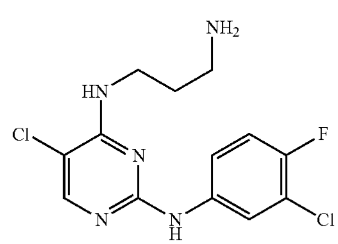 |
| (8) | 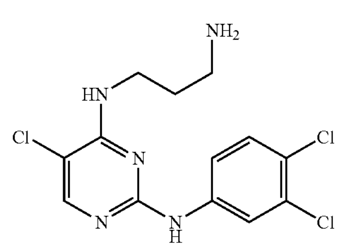 |

TABLE 1-continued
| Example | Chemical Structure |
|---|---|
| (9) | 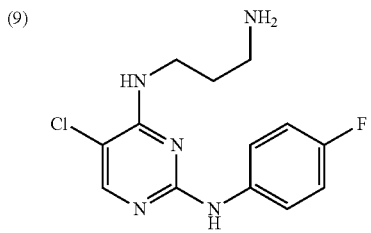 |
| (10) | 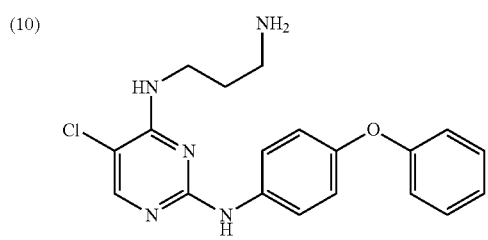 |
| (11) | 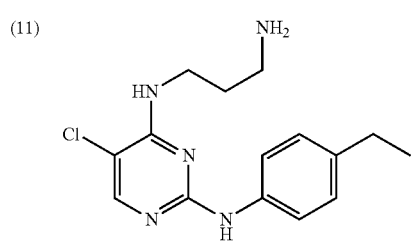 |
| (12) | 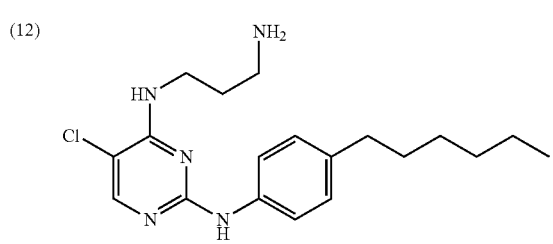 |
| (13) | 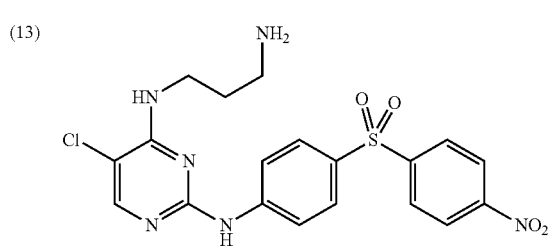 |
| (14) | 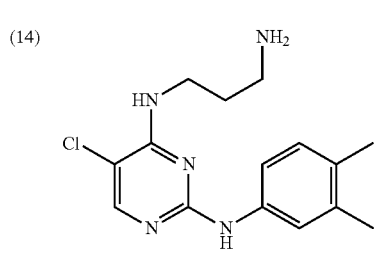 |
| (15) | 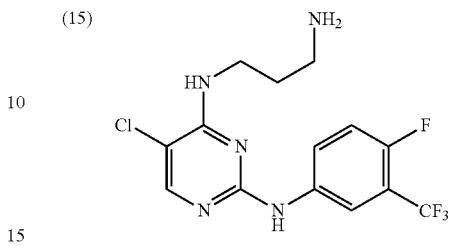 |
| (16) | 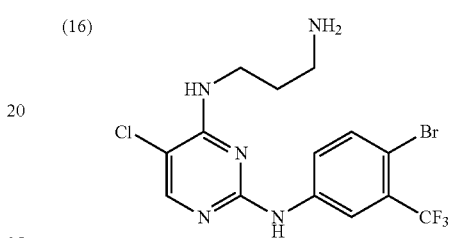 |
| (17) | 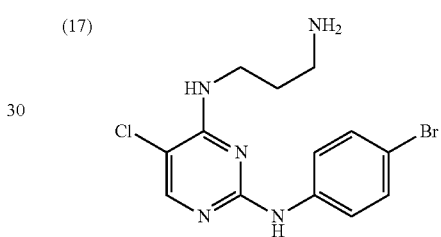 |
| (18) | 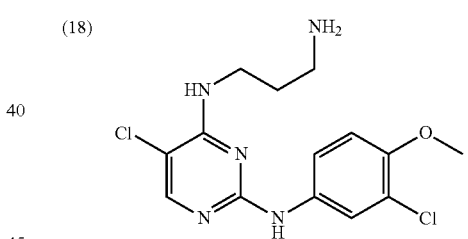 |
| (19) | 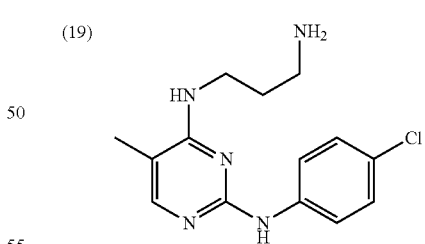 |
| (20) | 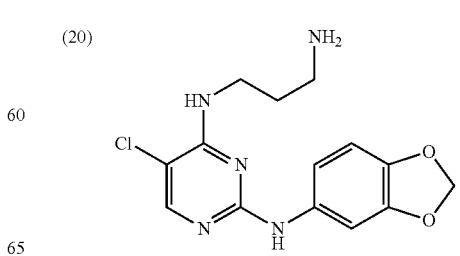 |

TABLE 1-continued

| Example | Chemical Structure |
|---|---|
| (21) | 5-chloro-N4-(3-aminopropyl)-N2-(2,3-dihydro-1H-inden-5-yl)pyrimidine-2,4-diamine |
| (22) | 5-chloro-N4-(3-aminopropyl)-N2-(2,3-dihydrobenzo[b][1,4]dioxin-6-yl)pyrimidine-2,4-diamine |
| (23) | 5-chloro-N4-(3-aminopropyl)-N2-(5,6,7,8-tetrahydronaphthalen-2-yl)pyrimidine-2,4-diamine |
| (24) | 5-chloro-N4-(3-aminopropyl)-N2-(1-oxo-1,2,3,4-tetrahydronaphthalen-6-yl)pyrimidine-2,4-diamine |
| (25) | 5-chloro-N4-(3-aminopropyl)-N2-(4-(piperazin-1-yl)phenyl)pyrimidine-2,4-diamine |
| (26) | 5-chloro-N4-(3-aminopropyl)-N2-(4-(piperidin-4-yl)phenyl)pyrimidine-2,4-diamine |

TABLE 1-continued

| Example | Chemical Structure |
|---|---|
| (27) | 5-methyl-N4-(3-aminopropyl)-N2-(3-chloro-4-methylphenyl)pyrimidine-2,4-diamine |
| (28) | 5-methyl-N4-(3-aminopropyl)-N2-(4-fluorophenyl)pyrimidine-2,4-diamine |
| (29) | 5-methyl-N4-(3-aminopropyl)-N2-(4-(piperazin-1-yl)phenyl)pyrimidine-2,4-diamine |
| (30) | 5-methyl-N4-(3-aminopropyl)-N2-(5,6,7,8-tetrahydronaphthalen-2-yl)pyrimidine-2,4-diamine |
| (31) | 5-methyl-N4-(3-aminopropyl)-N2-(4-fluoro-3-(trifluoromethyl)phenyl)pyrimidine-2,4-diamine |
| (32) | 5-methyl-N4-(3-aminopropyl)-N2-(4-bromo-3-(trifluoromethyl)phenyl)pyrimidine-2,4-diamine |

TABLE 1-continued
| Example | Chemical Structure |
|---|---|
| (33) | 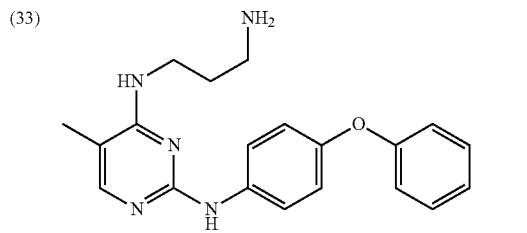 |
| (34) | 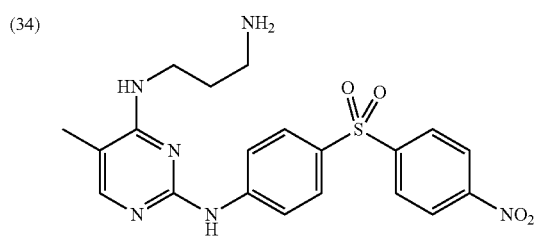 |
| (35) | 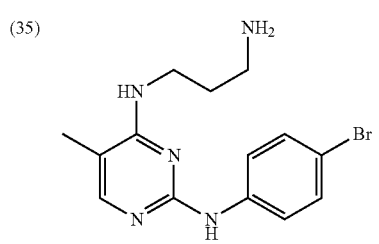 |
| (36) | 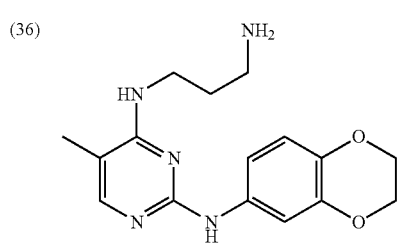 |
| (37) | 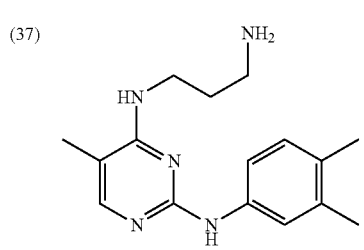 |
| (38) | 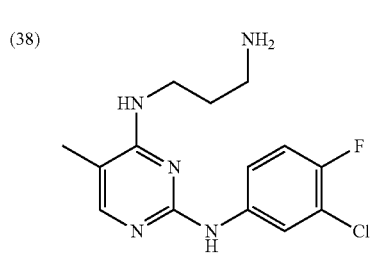 |
TABLE 1-continued
| Example | Chemical Structure |
|---|---|
| (39) | 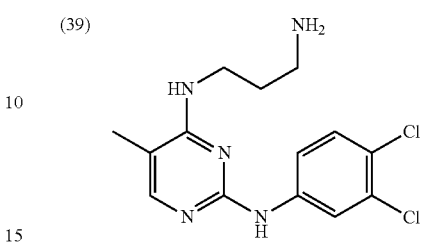 |
| (40) | 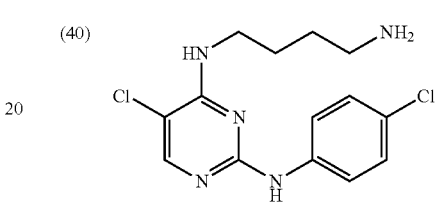 |
| (41) | 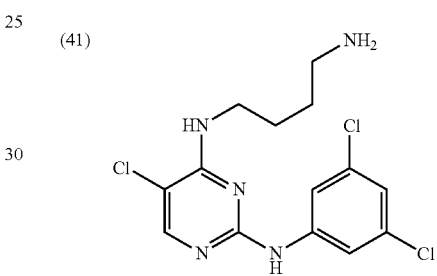 |
TABLE 2
| Comparative Example | Chemical Structure |
|---|---|
| (1) | 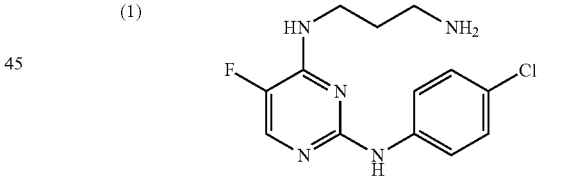 |
| (2) | 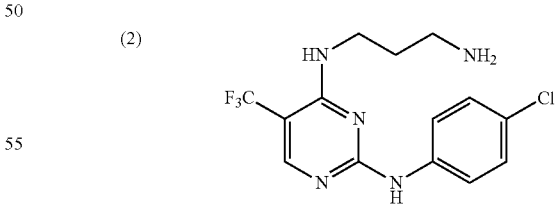 |
| (3) | 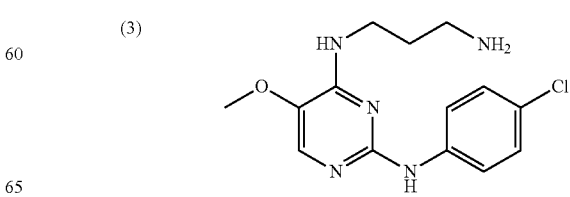 |

TABLE 2-continued

| Comparative Example | Chemical Structure |
|---|---|
| (4) | 4-HN-propyl-NH2, 2-(4-chlorophenylamino)pyrimidine |
| (5) | 4-HN-propyl-NH2, 5-O2N, 2-(4-chlorophenylamino)pyrimidine |
| (6) | 4-HN-propyl-NH2, 5-Br, 2-(4-chlorophenylamino)pyrimidine |
| (7) | 4-HN-ethyl-NH2, 5-Cl, 2-(4-chlorophenylamino)pyrimidine |
| (8) | 4-HN-ethyl-NH2, 5-methyl, 2-(4-chlorophenylamino)pyrimidine |

Experimental Example 1: Evaluation of DRAK1 and DARK2 Activity Inhibition 1-1. Experiment Preparation DRAK1 and DRAK2 recombinant proteins were purchased from SignalChem Inc. To measure the kinase enzyme activity, the ADP-Glo™ kit provided by Promega Inc. was used. Buffer A used in the kinase reaction was composed of 60 mM Tris-Cl (pH 7.5), 30 mM $MgCl_2$ and 0.15% BSA. Just before the experiment, 1 mM DTT was prepared by diluting 1 M solution and added thereto.

1-2. Experimental Method

To measure the DRAK1 and DRAK2 activity, the substrate MRCL3 peptide and ATP were mixed with the enzymes. After an appropriate period of time, the reaction product ADP was quantitatively analyzed.

The buffer solution A was used to make a 3× substrate solution of 3× concentration so that the final concentrations of ATP and MRCL3 peptides were 1 uM, respectively, and 2.5 µl of each solution was dispensed into Optiplate 384 (perkin-elmer) microplate.

The final concentrations of ATP and MRCL3 peptide were made to be 1 uM respectively by using buffer A, followed by preparing a 3× substrate solution. The prepared substrate solution was distributed in Optiplate 384 (Perkin-Elmer) microplate (2.5 ul/well). Then, the compounds of Examples 1~39 and the compounds of Comparative Examples 1-6, whose concentrations were tripled by the final concentration were distributed thereto (2.5 ul/well). Lastly, DRAK1 or DRAK2 enzyme solution, properly diluted by using buffer A, was added thereto (2.5 ul/well). Centrifugation was performed at 800 rpm for 1 minute, and then enzyme reaction was induced at 30° C.

2 hours later, the enzyme reaction was terminated. To eliminate residual ATP, ADP-Glo™ reagent contained in ADP-Glo™ was added to each well at the concentration of 7.5 ul, which was the same amount as the sum of the previously added reagents, followed by centrifugation at the same RPM and time as the above. Additional reaction was induced at room temperature for 40 minutes. To convert the ADP produced by the kinase activity to ATP, 15 ul of kinase detection buffer was added to each well, followed by centrifugation. Five minutes after the centrifugation was completed, the luminescence value of the reaction product was determined using Envision, and the enzyme activity inhibition effect of the compound was measured. Then, $IC_{50}$ of each compound was determined using Prism program.

1-3. Experiment Results

The DRAK1 and DRAK2 enzyme activity inhibition effects of the novel pyrimidine compounds and the comparative example compounds measured above are shown in Table 3 below.

TABLE 3

| Example | DRAK1 $IC_{50}$ (μM) | DRAK2 $IC_{50}$ (μM) |
|---|---|---|
| (1) | 0.41 | 0.038 |
| (2) | ND | 0.026 |
| (3) | 0.24 | 0.011 |
| (4) | ND | 0.08 |
| (5) | ND | 0.74 |
| (6) | 0.22 | 0.024 |
| (7) | 0.2 | 0.07 |
| (8) | 0.31 | 0.059 |
| (9) | 0.29 | 0.019 |
| (10) | 0.18 | 0.026 |
| (11) | 0.37 | 0.044 |
| (12) | 1.9 | 0.056 |
| (13) | 0.11 | 0.014 |
| (14) | 0.22 | 0.037 |
| (15) | 0.18 | 0.026 |
| (16) | 0.74 | 0.034 |
| (17) | 0.39 | 0.023 |
| (18) | 0.18 | 0.035 |
| (19) | 0.71 | 0.023 |
| (20) | 0.35 | 0.016 |
| (21) | 0.22 | 0.021 |
| (22) | 0.22 | 0.024 |
| (23) | 0.16 | 0.015 |
| (24) | 0.23 | 0.019 |
| (25) | 0.03 | 0.022 |
| (26) | ND | 0.019 |
| (27) | ND | 0.098 |
| (28) | ND | 0.19 |
| (29) | ND | 0.1 |
| (30) | ND | 0.16 |
| (31) | ND | 0.18 |
| (32) | ND | 1.4 |
| (33) | ND | 0.49 |
| (34) | ND | 0.34 |
| (35) | ND | 0.089 |
| (36) | ND | 0.11 |
| (37) | ND | 0.082 |
| (38) | ND | 0.035 |
| (39) | ND | 0.075 |

TABLE 3-continued

| Example | DRAK1 IC$_{50}$ (μM) | DRAK2 IC$_{50}$ (μM) |
|---|---|---|
| (40) | 0.48 | 0.047 |
| (41) | ND | 0.031 |
| Comparative Example 1 | ND | 0.3 |
| Comparative Example 2 | ND | 0.12 |
| Comparative Example 3 | ND | 0.87 |
| Comparative Example 4 | ND | 1.1 |
| Comparative Example 5 | ND | 0.32 |
| Comparative Example 6 | 0.04 | 0.027 |

(In table 3, ND means not determined).

As shown in Table 3, the compounds of Examples 1~41 of the present invention demonstrated excellent DRAK1 and DRAK2 inhibition activity. Some of the compounds of Comparative Examples also displayed excellent DRAK2 inhibition effect selectively.

Experimental Example 2: Evaluation of DRAK2 Selectivity

The following experiment was performed by the same manner as described in Experimental Example 1, in order to evaluate whether the compounds of Examples of the present invention had a better selectivity for DRAK2 than DRAK1. The compounds of Example 1 and Example 19 were used as the experimental group and the compound of Comparative Example 6 was used as the control. The results are shown in Table 4.

TABLE 4

| Experimental Group | DRAK1 IC$_{50}$ (μM) | DRAK2 IC$_{50}$ (μM) |
|---|---|---|
| Example 1 | 0.41 | 0.038 |
| Example 19 | 0.71 | 0.023 |
| Comparative Example 6 | 0.04 | 0.027 |

As shown in Table 4, the compound of Comparative Example 6 in which R$^1$ is Br in chemical formula 1 of the present invention displayed both DRAK1 and DRAK2 inhibition activity, while the compounds of Examples 1 and 19 of the present invention demonstrated DRAK2 inhibition activity only, indicating that the compounds had excellent DRAK2 selectivity.

Therefore, since the compounds of Examples of the present invention did not inhibit DRAK1 but demonstrated excellent inhibitory activity against DRAK2 only, it was remarkable that side effects caused by DRAK1 inhibition was able to be prevented.

On the other hand, the compounds represented by formula 1 of the present invention can be formulated into various forms according to the purpose.

The followings are examples of the formulation of the composition comprising the compound represented by formula 1 of the present invention as an active ingredient, but the present invention is not limited thereto.

Experimental Example 3: Evaluation of DRAK2 Inhibition Activity

To evaluate DRAK2 inhibition activity of the compound represented by formula 1 according to the number of n, the experiment was performed with the compounds of Example 1, Example 19, Example 40, Comparative Example 7 and Comparative Example 8 by the same manner as described in Experimental Example 1, leading to the measurement of IC$_{50}$ to DRAK2. The results are shown in Table 5.

TABLE 5

| Compound | DRAK2 IC$_{50}$ (μM) |
|---|---|
| Comparative Example 7 | 0.11 |
| Example 1 | 0.032 |
| Example 40 | 0.047 |
| Comparative Example 8 | 0.14 |
| Example 19 | 0.023 |

As shown in Table 5, the compounds of Examples 1, 19 and 40 in which n is 1 or 2 demonstrated significantly lower IC$_{50}$ than the compounds of Comparative Examples 7 and 8 in which n is 0.

Manufacturing Example 1: Preparation of Pharmaceutical Formulations 1-1. Preparation of Powders

| | |
|---|---|
| Compound of formula 1 | 500 mg |
| Lactose | 100 mg |
| Talc | 10 mg |

Powders were prepared by mixing all the above components, which were filled in airtight packs according to the conventional method for preparing powders.

1-2. Preparation of Tablets

| | |
|---|---|
| Compound of formula 1 | 500 mg |
| Corn starch | 100 mg |
| Lactose | 100 mg |

Magnesium stearate 2 mg

Tablets were prepared by mixing all the above components by the conventional method for preparing tablets.

1-3. Preparation of Capsules

| | |
|---|---|
| Compound of formula 1 | 500 mg |
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

1-4. Preparation of Injectable Solutions

| | |
|---|---|
| Compound of formula 1 | 500 mg |
| Sterilized distilled water | proper amount |
| pH regulator | proper amount |

Injectable solutions were prepared by mixing all the above components, putting the mixture into 2 ml ampoules and sterilizing thereof by the conventional method for preparing injectable solutions.

1-4. Preparation of Liquid Formulations

| | |
|---|---|
| Compound of formula 1 | 100 mg |
| Isomerized sugar | 10 g |
| Mannitol | 5 g |

Purified water proper amount

All the above components were dissolved in purified water. After adding lemon flavor, total volume was adjusted to be 100 ml by adding purified water. Liquid formulations were prepared by putting the mixture into brown bottles and sterilizing thereof by the conventional method for preparing liquid formulations.

INDUSTRIAL APPLICABILITY

The novel pyrimidine compounds of the present invention significantly inhibit the activity of DRAK known to interfere the TGF-β signal transduction system playing a role in inhibiting cancer growth. Therefore, it can be used as a pharmaceutical composition for preventing or treating cancer and inflammatory disease.

What is claimed is:

1. A compound represented by Formula 1:

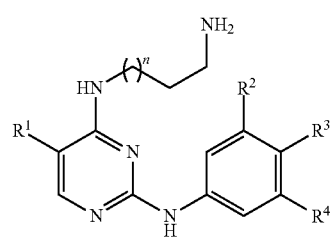

Formula 1 or a pharmaceutically acceptable salt thereof,
wherein:
$R^1$ is chloro or methyl;
$R^2$ is hydrogen or chloro;
$R^3$ is hydrogen, fluoro, chloro, bromo, methyl, ethyl, isopropyl, pentyl, hexyl, octyl, methoxy, phenoxy, (4-nitrophenyl)sulfonyl, piperidin-4-yl, or piperazin-1-yl;
$R^4$ is hydrogen, chloro, methyl, trifluoromethyl, phenoxy, (4-nitrophenyl)sulfonyl, or piperidin-4-yl; or
$R^3$ and $R^4$, together with the carbons to which they are attached, form a fused ring selected form the group consisting of:

and
n is 1 or 2.

2. The compound according to claim 1, wherein the compound is selected from the group consisting of:
(1) $N^4$-(3-aminopropyl)-5-chloro-$N^2$-(4-chlorophenyl)pyrimidine-2,4-diamine;
(2) $N^4$-(3-aminopropyl)-5-chloro-$N^2$-(3,5-dichlorophenyl)pyrimidine-2,4-diamine;
(3) $N^4$-(3-aminopropyl)-5-chloro-$N^2$-(4-isopropylphenyl)pyrimidine-2,4-diamine;
(4) $N^4$-(3-aminopropyl)-5-chloro-$N^2$-(4-pentylphenyl)pyrimidine-2,4-diamine;
(5) $N^4$-(3-aminopropyl)-5-chloro-$N^2$-(4-octylphenyl)pyrimidine-2,4-diamine;
(6) $N^4$-(3-aminopropyl)-5-chloro-$N^2$-(3-chloro-4-methylphenyl)pyrimidine-2,4-diamine;
(7) $N^4$-(3-aminopropyl)-5-chloro-$N^2$-(3-chloro-4-fluorophenyl)pyrimidine-2,4-diamine;
(8) $N^4$-(3-aminopropyl)-5-chloro-$N^2$-(3,4-dichlorophenyl)pyrimidine-2,4-diamine;
(9) $N^4$-(3-aminopropyl)-5-chloro-$N^2$-(4-fluorophenyl)pyrimidine-2,4-diamine;

(10) $N^4$-(3-aminopropyl)-5-chloro-$N^2$-(4-phenoxyphenyl)pyrimidine-2,4-diamine;
(11) $N^4$-(3-aminopropyl)-5-chloro-$N^2$-(4-ethylphenyl)pyrimidine-2,4-diamine;
(12) $N^4$-(3-aminopropyl)-5-chloro-$N^2$-(4-hexylphenyl)pyrimidine-2,4-diamine;
(13) $N^4$-(3-aminopropyl)-5-chloro-$N^2$-(4-(4-nitrophenylsulfonyl)phenyl)pyrimidine-2,4-diamine;
(14) $N^4$-(3-aminopropyl)-5-chloro-$N^2$-(3,4-dimethylphenyl)pyrimidine-2,4-diamine
(15) $N^4$-(3-aminopropyl)-5-chloro-$N^2$-(4-fluoro-3-(trifluoromethyl)phenyl)pyrimidine-2,4-diamine;
(16) $N^4$-(3-aminopropyl)-$N^2$-(4-bromo-3-(trifluoromethyl)phenyl)-5-chloropyrimidine-2,4-diamine;
(17) $N^4$-(3-aminopropyl)-$N^2$-(4-bromophenyl)-5-chloropyrimidine-2,4-diamine;
(18) $N^4$-(3-aminopropyl)-5-chloro-$N^2$-(3-chloro-4-methoxyphenyl)pyrimidine-2,4-diamine;
(19) $N^4$-(3-aminopropyl)-$N^2$-(4-chlorophenyl)-5-methylpyrimidine-2,4-diamine;
(20) $N^4$-(3-aminopropyl)-$N^2$-(benzo[d][1,3]dioxol-5-yl)-5-chloropyrimidine-2,4-diamine;
(21) $N^4$-(3-aminopropyl)-5-chloro-$N^2$-(2,3-dihydro-1H-indene-5-yl)pyrimidine-2,4-diamine;
(22) $N^4$-(3-aminopropyl)-5-chloro-$N^2$-(2,3-dihydrobenzo[b][1,4]dioxin-6-yl)pyrimidine-2,4-diamine;
(23) $N^4$-(3-aminopropyl)-5-chloro-$N^2$-(5,6,7,8-tetrahydronaphthalene-2-yl)pyrimidine-2,4-diamine;
(24) 6-(4-(3-aminopropylamino)-5-chloropyrimidine-2-ylamino)-3,4-dihydronaphthalene-1(2H)-one;
(25) $N^4$-(3-aminopropyl)-5-chloro-$N^2$-(4-(piperazine-1-yl)phenyl)pyrimidine-2,4-diamine;
(26) $N^4$-(3-aminopropyl)-5-chloro-$N^2$-(4-(piperidine-4-yl)phenyl)pyrimidine-2,4-diamine;
(27) $N^4$-(3-aminopropyl)-$N^2$-(3-chloro-4-methylphenyl)-5-methylpyrimidine-2,4-diamine;
(28) $N^4$-(3-aminopropyl)-$N^2$-(4-fluorophenyl)-5-methylpyrimidine-2,4-diamine;
(29) $N^4$-(3-aminopropyl)-5-methyl-$N^2$-(4-(piperazine-1-yl)phenyl)pyrimidine-2,4-diamine;
(30) $N^4$-(3-aminopropyl)-5-methyl-$N^2$-(5,6,7,8-tetrahydronaphthalene-2-yl)pyrimidine-2,4-diamine;
(31) $N^4$-(3-aminopropyl)-$N^2$-(4-fluoro-3-(trifluoromethyl)phenyl)-5-methylpyrimidine-2,4-diamine;
(32) $N^4$-(3-aminopropyl)-$N^2$-(4-bromo-3-(trifluoromethyl)phenyl)-5-methylpyrimidine-2,4-diamine;
(33) $N^4$-(3-aminopropyl)-5-methyl-$N^2$-(4-phenoxyphenyl)pyrimidine-2,4-diamine;
(34) $N^4$-(3-aminopropyl)-5-methyl-$N^2$-(4-(4-nitrophenylsulfonyl)phenyl)pyrimidine-2,4-diamine;
(35) $N^4$-(3-aminopropyl)-$N^2$-(4-bromophenyl)-5-methylpyrimidine-2,4-diamine;
(36) $N^4$-(3-aminopropyl)-$N^2$-(2,3-dihydrobenzo[b][1,4]dioxin-6-yl)-5-methylpyrimidine-2,4-diamine;
(37) $N^4$-(3-aminopropyl)-$N^2$-(3,4-dimethylphenyl)-5-methylpyrimidine-2,4-diamine;
(38) $N^4$-(3-aminopropyl)-$N^2$-(3-chloro-4-fluorophenyl)-5-methylpyrimidine-2,4-diamine;
(39) $N^4$-(3-aminopropyl)-$N^2$-(3,4-dichlorophenyl)-5-methylpyrimidine-2,4-diamine;
(40) $N^4$-(4-n-aminobutyl)-$N^2$-(4-chlorophenyl)-5-chloropyrimidine-2,4-diamine; and
(41) $N^4$-(4-n-aminobutyl)-$N^2$-(3,5-dichlorophenyl)-5-chloropyrimidine-2,4-diamine.

3. A pharmaceutical composition comprising the compound according to claim 1, or a pharmaceutically acceptable salt thereof, as an active ingredient and a pharmaceutically acceptable excipient or diluent.

4. A method for inhibiting death-associated protein-kinase-related apoptosis kinase activity in a subject having cancer, comprising administering to the subject in need thereof the compound according to claim 1, or pharmaceutically acceptable salt thereof.

5. A method for inhibiting death-associated protein-kinase-related apoptosis kinase activity in a subject having cancer, comprising administering to the subject in need thereof the pharmaceutical composition according to claim 3.

6. A method for inhibiting death-associated protein-kinase-related apoptosis kinase activity in a subject having an inflammatory disease, comprising administering to the subject in need thereof the pharmaceutical composition according to claim 3.

7. The method according to claim 4, wherein the cancer is one or more cancers selected from the group consisting of pseudomyxoma, intrahepatic cholangiocarcinoma, hepatoblastoma, liver cancer, thyroid cancer, colon cancer, testicular cancer, myelodysplastic syndrome, glioblastoma, oral cancer, lip cancer, mycosis fungoides, acute myelogenous leukemia, acute lymphocytic leukemia, basal cell carcinoma, ovarian epithelial cancer, ovarian germ cell carcinoma, male breast cancer, brain cancer, pituitary adenoma, multiple myeloma, gallbladder cancer, biliary cancer, colon cancer, chronic myelogenous leukemia, chronic lymphocytic leukemia, retinoblastoma, choroidal melanoma, diffuse large B cell lymphoma, ampulla of Vater cancer, bladder cancer, peritoneal cancer, parathyroid cancer, adrenal gland cancer, sinunasal cancer, non-small cell lung cancer, non-Hodgkin's lymphoma, tongue cancer, astrocytoma, small cell lung cancer, pediatric brain cancer, pediatric lymphoma, childhood leukemia, small bowel cancer, meningioma, esophagus cancer, glioma, neuroblastoma, renal cancer, kidney cancer, heart cancer, duodenal cancer, malignant soft tissue tumor, malignant bone cancer, malignant lymphoma, malignant mesothelioma, malignant melanoma, eye cancer, vulvar cancer, ureteral cancer, urethral cancer, cancer of unknown primary site, gastric lymphoma, gastric cancer, gastric carcinoid, gastrointestinal stromal cancer, Wilms' tumor, breast cancer, sarcoma, penile cancer, pharyngeal cancer, getstational trophoblatic disease, cervical cancer, endometrial cancer, uterine sarcoma, prostate cancer, metastatic bone cancer, metastatic brain cancer, mediastinal cancer, rectal cancer, rectal carcinoid, vaginal cancer, spinal cord cancer, vestibular schwannoma, pancreatic cancer, salivary gland cancer, Kaposi's sarcoma, Paget's disease, tonsil cancer, squamous cell carcinoma, adenocarcinoma of lung, lung cancer, squamos cell carcinoma of lung, skin cancer, anal cancer, rhabdomyosarcoma, laryngeal cancer, pleural cancer, and thymus cancer.

8. The method according to claim 5, wherein the cancer is one or more cancers selected from the group consisting of pseudomyxoma, intrahepatic cholangiocarcinoma, hepatoblastoma, liver cancer, thyroid cancer, colon cancer, testicular cancer, myelodysplastic syndrome, glioblastoma, oral cancer, lip cancer, mycosis fungoides, acute myelogenous leukemia, acute lymphocytic leukemia, basal cell carcinoma, ovarian epithelial cancer, ovarian germ cell carcinoma, male breast cancer, brain cancer, pituitary adenoma, multiple myeloma, gallbladder cancer, biliary cancer, colon cancer, chronic myelogenous leukemia, chronic lymphocytic leukemia, retinoblastoma, choroidal melanoma, diffuse large B cell lymphoma, ampulla of Vater cancer, bladder cancer, peritoneal cancer, parathyroid cancer, adrenal gland cancer, sinunasal cancer, non-small cell lung cancer, non-Hodgkin's lymphoma, tongue cancer, astrocytoma, small cell lung cancer, pediatric brain cancer, pediatric lymphoma, childhood leukemia, small bowel cancer, meningioma, esophagus cancer, glioma, neuroblastoma, renal cancer, kidney cancer, heart cancer, duodenal cancer, malignant soft tissue tumor, malignant bone cancer, malignant lymphoma, malignant mesothelioma, malignant melanoma, eye cancer, vulvar cancer, ureteral cancer, urethral cancer, cancer of unknown primary site, gastric lymphoma, gastric cancer, gastric carcinoid, gastrointestinal stromal cancer, Wilms' tumor, breast cancer, sarcoma, penile cancer, pharyngeal cancer, getstational trophoblastic disease, cervical cancer, endometrial cancer, uterine sarcoma, prostate cancer, metastatic bone cancer, metastatic brain cancer, mediastinal cancer, rectal cancer, rectal carcinoid, vaginal cancer, spinal cord cancer, vestibular schwannoma, pancreatic cancer, salivary gland cancer, Kaposi's sarcoma, Paget's disease, tonsil cancer, squamous cell carcinoma, adenocarcinoma of lung, lung cancer, squamos cell carcinoma of lung, skin cancer, anal cancer, rhabdomyosarcoma, laryngeal cancer, pleural cancer, and thymus cancer.

9. The method according to claim 6, wherein the inflammatory disease is one or more diseases selected from the group consisting of inflammatory colitis of autoimmune diseases, Crohn's disease, Behcet's disease, multiple sclerosis, macular degeneration, arthritis, type 1 diabetes, encephalitis and viral meningitis.

10. A process for preparing a compound represented by Formula 1:

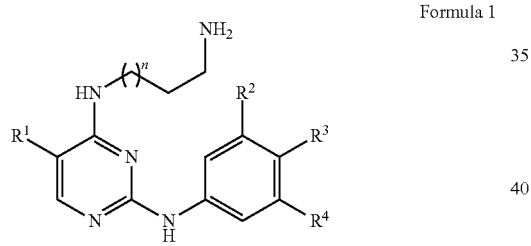

Formula 1 wherein:
R$^1$ is chloro or methyl;
R$^2$ is hydrogen or chloro;
R$^3$ is hydrogen, fluoro, chloro, bromo, methyl, ethyl, isopropyl, pentyl, hexyl, octyl, methoxy, phenoxy, (4-nitrophenyl)sulfonyl, piperidin-4-yl, or piperazin-1-yl;
R$^4$ is hydrogen, chloro, methyl, trifluoromethyl, phenoxy, (4-nitrophenyl)sulfonyl, or piperidin-4-yl; or
R$^3$ and R$^4$, together with the carbons to which they are attached, form a fused ring selected from the group consisting of:

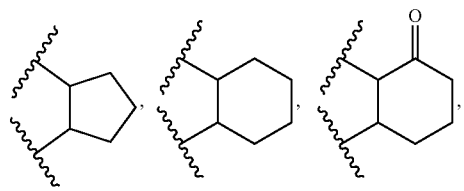

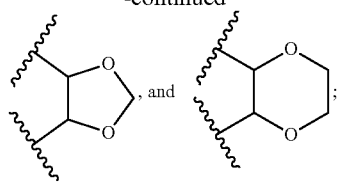

and
n is 1 or 2;
wherein the process comprises:
(1) reacting a compound represented by Formula 2:

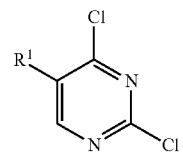

Formula 2 wherein:
R$^1$ is chloro or methyl;
with a compound represented by Formula 3:

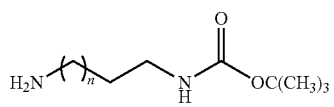

Formula 3 wherein:
n is 1 or 2;
to provide a compound represented by Formula 4:

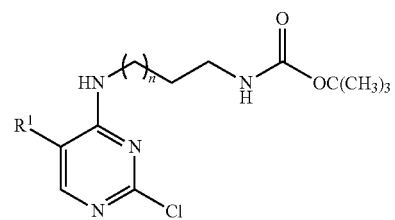

Formula 4 wherein:
R$^1$ is chloro or methyl; and
n is 1 or 2; and
(2) reacting the compound represented by Formula 4 above with a compound represented by Formula 5:

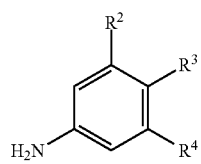

Formula 5 wherein

R² is hydrogen or chloro;

R³ is hydrogen, fluoro, chloro, bromo, methyl, ethyl, isopropyl, pentyl, hexyl, octyl, methoxy, phenoxy, (4-nitrophenyl)sulfonyl, piperidin-4-yl, or piperazin-1-yl;

R⁴ is hydrogen, chloro, methyl, trifluoromethyl, phenoxy, (4-nitrophenyl)sulfonyl, or piperidin-4-yl; or R³ and R⁴, together with the carbons to which they are attached, form a fused ring selected from the group consisting of:

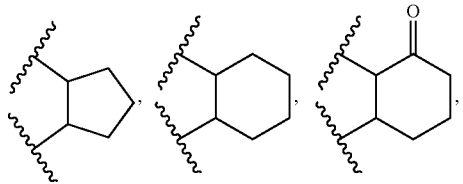

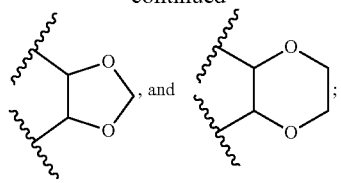

in the presence of an acid, to provide the compound represented by Formula 1:

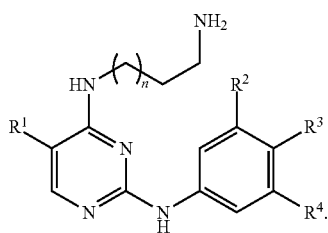

Formula 1

* * * * *